United States Patent [19]

Persello

[11] Patent Number: 5,614,176

[45] Date of Patent: Mar. 25, 1997

[54] DENTIFRICE-COMPATIBLE SILICA PARTICULATES

[75] Inventor: Jacques Persello, Montluel, France

[73] Assignee: Rhone-Poulenc Chimie, Courbevoie Cedex, France

[21] Appl. No.: 485,512

[22] Filed: Jun. 7, 1995

Related U.S. Application Data

[62] Division of Ser. No. 141,337, Oct. 26, 1993, which is a division of Ser. No. 901,078, Jun. 19, 1992, Pat. No. 5,286,478, which is a continuation-in-part of Ser. No. 261,935, Oct. 25, 1988, abandoned, Ser. No. 261,936, Oct. 25, 1988, abandoned, Ser. No. 518,764, May 3, 1990, abandoned, and Ser. No. 518,765, May 3, 1990, abandoned.

[30] Foreign Application Priority Data

| Nov. 4, 1987 | [FR] | France | 8715275 |
| Nov. 4, 1987 | [FR] | France | 8715276 |
| May 3, 1989 | [FR] | France | 8905868 |
| May 3, 1989 | [FR] | France | 8905869 |

[51] Int. Cl.$^6$ .............................. A61K 7/16; A61K 7/18
[52] U.S. Cl. .............................. 424/57; 424/49; 424/52; 423/335; 423/338; 106/35; 106/492; 51/308
[58] Field of Search .............................. 424/49, 52, 57; 51/308; 423/335, 338; 106/35, 492

[56] References Cited

U.S. PATENT DOCUMENTS

| 3,070,426 | 12/1962 | Winyall . | |
| 3,794,712 | 2/1974 | Aboutboul et al. | 423/338 |
| 3,800,031 | 3/1974 | Sale et al. | 423/338 |
| 3,803,046 | 4/1974 | Winyall et al. | 252/315.6 |
| 3,893,840 | 7/1975 | Wason | 106/492 |
| 3,988,162 | 10/1976 | Wason | 106/492 |
| 4,015,996 | 4/1977 | Wason | 106/431 |
| 4,040,858 | 8/1977 | Wason | 106/466 |
| 4,045,240 | 8/1977 | Wason et al. | 424/335 |
| 4,049,781 | 9/1977 | Acker et al. | 423/338 |
| 4,105,757 | 8/1978 | Wason | 424/49 |
| 4,144,321 | 3/1979 | Wason . | |
| 4,191,742 | 3/1980 | Wason et al. . | |
| 4,216,113 | 8/1980 | Winyall | 523/210 |
| 4,251,281 | 2/1981 | Machurat et al. . | |
| 4,272,509 | 6/1981 | Wason . | |
| 4,279,766 | 7/1981 | Joubert et al. . | |
| 4,331,706 | 5/1982 | Kindrick . | |
| 4,340,583 | 6/1982 | Wason | 424/49 |
| 4,422,880 | 12/1983 | Wason et al. . | |
| 4,562,065 | 12/1985 | Hayes et al. . | |
| 4,562,066 | 8/1991 | Hayes et al. | 424/52 |
| 4,581,292 | 4/1986 | Shinpo et al. . | |
| 4,590,052 | 5/1986 | Chevallier et al. | 424/335 |
| 4,676,964 | 6/1987 | Seki et al. | 423/335 |
| 4,704,425 | 11/1987 | Lagarde et al. | 524/492 |
| 4,874,594 | 10/1989 | Chevallier | 423/335 |
| 4,956,167 | 9/1990 | Aldcroft et al. | 423/339 |
| 4,973,462 | 11/1990 | Akira et al. | 423/339 |

FOREIGN PATENT DOCUMENTS

| 31271 | 4/1963 | European Pat. Off. . |
| 46057 | 2/1982 | European Pat. Off. . |
| 1327033 | 4/1963 | France . |
| 1667701 | 5/1972 | Germany . |
| 2544218 | 4/1977 | Germany . |
| 2920906A1 | 11/1979 | Germany . |
| 3525802 | 4/1987 | Germany . |
| 60-204613 | 3/1984 | Japan . |
| 6256319 | 9/1985 | Japan . |
| 1580672 | 12/1980 | United Kingdom . |

*Primary Examiner*—Carlos A. Azpuru
*Attorney, Agent, or Firm*—Burns, Doane, Swecker & Mathis, L.L.P.

[57] ABSTRACT

Novel silica particulates especially adapted for formulation to dentifrice compositions exhibit unique physical and chemical properties. In one embodiment, silica particulates have a unique surface chemistry as to be at least 50% compatible with zinc values, and have a number of OH functions, expressed as OH/nm$^2$, of at most 15 and a zero charge point (PZC) of from 3 to 6.5. In a second embodiment, particulates have a surface chemistry as to be at least 65%, and preferably at least 90% compatible with guanidine values, notably chlorhexidine, and acidity function thereof, Ho, of at least 3.3. In a third embodiment, silica particulates are compatible with organic amines, and have a pH, in aqueous suspension, which varies according to the equations pH≦7.5–0.7 log(C) and pH≧5.0–0.5 log(C) and which also varies as a function of the electrical conductivity thereof, according to the equations pH≦8.5–0.4 log(D) and pH≧7.0–0.6 log(D) wherein (C) represents the weight concentration of said silica suspension, expressed % SiO$_2$ and (D) represents the electrical conductivity of such aqueous silica suspension expressed in microsiemens.cm$^{-1}$. In a fourth embodiment, novel silica particulates are compatible with such metal cations as zinc, tin, strontium, and the like, as well as with the fluorides, and have a unique surface chemistry such that the number of OH$^-$ functions thereof, expressed in OH$^-$/nm$^2$, is equal to or less than 10, and also have a zero charge point (ZCP) ranging from 3 to 6.5 and a pH, in aqueous suspension, which varies as a function of the electrical conductivity thereof according to the equation pH=b–a log (D) in which a is a constant equal to or less than 0.6; b is a constant equal to or less than 8.5; and (D) represents the electrical conductivity of such aqueous silica suspension, expressed in microsiemens.cm$^{-1}$.

6 Claims, No Drawings

DENTIFRICE-COMPATIBLE SILICA PARTICULATES

This application is a divisional, of application Ser. No. 08/141,337, filed Oct. 26, 1993, now allowed a divisional of application Ser. No. 07/901,078, filed Jun. 19, 1992 now U.S. Pat. No. 5,286,478, which is a Continuation-in-Part of application Ser. Nos. 07/261,935 and 07/261,936, both filed Oct. 25, 1988 both abandoned, and application Ser. Nos. 07/518,764 and 07/518,765, both filed May 3, 1990 both abandoned.

CROSS-REFERENCE TO COMPANION APPLICATION

My copending application Ser. No. 07/353,528, filed May 18, 1989, assigned to the assignee hereof.

BACKGROUND OF THE INVENTION

1. Field of the Invention

The present invention relates to novel silica particulates especially well adapted for incorporation into dentifrice compositions, to a process for the production of such novel particulates, and to improved dentifrice compositions comprising same.

2. Description of the Prior Art

It is known to this an that silica is a useful material for incorporation into dentifrice compositions. It performs a variety of different functions therein.

Firstly, it serves as an abrasive agent, thus mechanically contributing to the elimination of dental plaque.

It may also serve as a thickening agent to impart particular rheological properties to the dentifrice, as well as a colorant to impart particular coloration to the composition.

It is also known to this an that dentifrices contain various active agents, in particular for the prevention of dental caries, to reduce the formation of dental plaque or the deposition of tartar on the teeth. Among such agents, the fluorides and the zinc compounds are especially representative. Other elements are also incorporated, such as phosphates, pyrophosphates, polyphosphates, polyphosphonates, guanidines, in particular the bisbiguanides, and one of the compounds most typically included is chlorhexidine. Dentifrice formulations may also contain flavorants, perfumes, and the like.

The dentifrice compositions can also contain organic amino compounds. By the term "organic amino compounds" is intended any active molecule present in the dentifrice formulation and containing at least one nitrogen atom. Particularly representative of such organic amino compounds are (1) the fluorine-containing amines useful for caries prophylaxis and especially long-chain amino acid or amino addition products with hydrogen fluoride, such as cetyl amine hydrofluoride, bis-(hydroxyethyl)-aminopropyl-N-hydroxyethyl octadecyl amine dihydrofluoride, octadecyl amine fluoride and N,N',N'-tri-(polyoxyethylene)-N-hexadecyl propylene diamene dihydrofluoride; (2) amino oxides useful as nonionic surfactants prepared by oxidation of tertiary aliphatic amines with hydrogen peroxide, especially the alkyl amine oxides of the formula $R(CH_3)_2N \rightarrow O$, in which R is a straight or branched chain alkyl radical having approximately 10 to 24 carbon atoms, and the amine oxides of the formula $R(CH_2CH_2OH)_2N \rightarrow O$, in which R is as defined above; (3) alkyl amines, which can be primary, secondary, tertiary or quaternary aliphatic amines useful as cationic surfactants, such as those of the formula $R-CH_2NH_2$, or dimethyl alkyl amines of the formula $R-N(CH_3)_2$ and cetyl trimethyl ammonium bromide; and (4) alkyl betaines, which are N-alkyl derivatives of N-dimethyl glycine and alkyl amidoalkyl betaines, designated hereinafter as "alkyl betaines".

Exemplary of this class of amphoteric surfactants are the alkyl betaines of the formula:

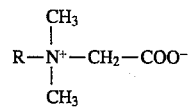

and the alkyl amidopropyl dimethyl betaines of the formula:

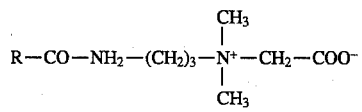

wherein R is a straight or branched chain alkyl radical having 10 to 24 carbon atoms.

A certain number of metal cations can be present in dentifrice compositions. Exemplary thereof are the alkaline earth metal cations, particularly calcium, strontium, barium, cations of Group IIIa, aluminum, indium, cations of Group IVa, germanium, tin, lead and cations of Group VIII, manganese, iron, nickel, zinc, titanium, zirconium, palladium, and the like. Such cations can be in the form of inorganic salts, e.g., the chloride, fluoride, nitrate, phosphate or sulfate, or in the form of organic salts, such as the acetate, citrate, and the like.

More specific examples of such salts are zinc citrate, zinc sulfate, strontium chloride, tin fluoride in the form of the single salt ($SnF_2$) or the double salt ($SnF_2/KF$), stannous chlorofluoride SnClF and zinc fluoride ($ZnF_2$).

The presence of the above-mentioned agents in the dentifrice presents the problem of their compatibility with silica. In effect, due particularly to its absorbent properties, the latter may have a tendency to react-with these agents such that they are no longer available to elicit their aforesaid therapeutic and/or useful responses.

French Patent Application 87/15,276 describes silica particulates compatible with zinc. However, the silicas described do not exhibit a completely adequate compatibility with other metal cations, such as tin, strontium, and the like.

SUMMARY OF THE INVENTION

Accordingly, a major object of the present invention is the provision of a novel silica material that is improvedly compatible with the typical dentifrice additives: the zinc compounds; the guanidines, particularly the bis-biguanidines, the most representative of which is chlorhexidine; and the aforementioned organic amino compounds, particularly the class of fluorine-containing amines and betanes.

Another object of the present invention is the provision of a novel silica material having improved compatibility with the various cations typically present in dentifrice formulations, such as zinc, strontium, tin, etc.

Another object of the present invention is the provision of processes for the preparation of such improvedly compatible silica particulates.

Another object of the present invention is the provision of a novel silica material that is also compatible with the fluoride anion. As enhanced compatibility with metal cations characteristically reduces compatibility with the fluoride anion, it is therefore particularly advantageous that the novel silica material of this invention remains compatible with the fluoride anion which is present in virtually all dentifrice compositions.

It has now unexpectedly been determined that the desired compatibility essentially depends on the surface chemistry of the silica particles. Indeed, it has now been established that there must exist a certain number of conditions with respect to the surface of the silica particles to ensure that they are compatible. According to a first embodiment of the present invention the silica particulates are characterized in that they display compatibility with zinc compounds of at least 50%, and have a number of OH functions, expressed as $OH/nm^2$, of at most 15 and a zero charge point (PZC) ranging from 3 to 6.5.

In a process embodiment specific to this first embodiment, the novel silica particulates are prepared by reacting a silicate with an acid, whereby a suspension or gel of the silica is produced, then separating and drying the silica, and thereafter washing the separated silica cake with water, followed by a second washing or a treatment with an acid solution.

The silica particulates according to a second embodiment of the present invention are characterized in that they display compatibility with compounds of the guanidine type, and in particular chlorhexidine, of at least 65% and more preferably at least 90%.

Furthermore, the silica particulates of this second embodiment, which are compatible with compounds of the guanidine type and in particular with chlorhexidine, are also characterized in that they have a surface chemistry such that the acidity function Ho thereof is at least 3.3.

In a process embodiment, the novel silica particulates are prepared by reacting a silicate with an acid, whereby a suspension or a gel of silica is produced, then separating and drying the silica, and thereafter washing the separated silica cake with water, until the conductivity of the filtrate is at the most 200 microsiemens.cm$^{-1}$.

A third embodiment of the invention features novel silica particulates, improvedly compatible with the class of fluorine-containing amines and betaines. These particulates are distinguished as having a surface chemistry such that, in aqueous suspension, the pH thereof varies as a function of its concentration in the area defined by the two inequations:

$$pH \leq 7.5 - 0.7 \log (C) \qquad \text{(Ia)}$$

and $$pH \geq 5.0 - 0.5 \log (C) \qquad \text{(Ib)}$$

and the pH thereof also varying as a function of its electrical conductivity in the area defined by the two inequations:

$$pH \leq 8.5 - 0.4 \log (D) \qquad \text{(IIa)}$$

and $$pH \geq 7.0 - 0.6 \log (D) \qquad \text{(IIb)}$$

wherein inequations (Ia) and (Ib), (C) represents the weight concentration of the aqueous silica suspension, expressed in % $SiO_2$; and wherein inequations (IIa) and (IIb), (D) represents the electrical conductivity of the aqueous silica suspension, expressed in microsiemens.cm$^{-1}$.

The novel silica particulates of this third embodiment of the invention also have an acidity function Ho of at least 4.0, a number of OH$^-$ sites per nm$^2$ equal to or below 12, and a zero charge point (ZCP) of at least 4.

This third embodiment also features novel silica particulates displaying a compatibility of at least 30% with organic amino compounds, more particularly at least 50% compatibility and preferably at least 80% compatibility with such organic amino compounds as fluorine-containing amines, amine oxides, alkyl amines and alkyl betaines.

This third embodiment also features novel silica particulates displaying a compatibility of at least 50%, more particularly at least 70%, with metal cations.

This third embodiment also features novel silica particulates displaying a compatibility with compounds of guanidine type, in particular chlorhexidine, of at least 30% and more particularly at least 60%.

The third embodiment also features a process for the preparation of such novel silica particulates, comprising reacting a silicate with an acid to produce a silica suspension or a silica gel, next conducting a first aging step at a pH equal to or above 6 and equal to or below 8.5, followed by a second aging at a pH equal to or below 6 and then a third aging step at a pH equal to or below 5, next separating the silica and washing it with water to such extent that an aqueous suspension is produced having a pH, measured on a 20% $SiO_2$ suspension, in accordance with the following equation:

$$pH = d - e \log (D) \qquad \text{(III)}$$

in which e is a constant equal to or greater than 0.6 and equal to or less than 1.0; d is a constant equal to or greater than 7.0 and equal to or less than 8.5; and (D) represents the electrical conductivity of the aqueous silica suspension, expressed in microsiemens.cm$^1$, and lastly drying such aqueous suspension.

A fourth embodiment of the present invention features silica particulates improvedly compatible with zinc and other metal cations, which are characterized in that they have a surface chemistry such that the number of OH$^-$ functions thereof, expressed in OH$^-$/nm$^2$, is equal to or less than 10, that its zero charge point (ZCP) ranges from 3 to 6.5 and that, in aqueous suspension, the pH thereof varies as a function of its electrical conductivity according to the following equation (I):

$$pH = b - a \log (D) \qquad \text{(I)}$$

wherein a is a constant equal to or less than 0.6; b is a constant equal to or less than 8.5; and (D) represents the electrical conductivity of the aqueous silica suspension, expressed in microsiemens.cm$^{-1}$.

The novel silica particulates of this fourth embodiment display at least 30% compatibility with at least one divalent and higher valency metal cation selected from Groups IIa, IIIa, IVa and VIII of the Periodic Table, more particularly at least 50% compatibility and preferably at least 80% compatibility.

The fourth embodiment also features a process for the preparation of such novel silica particulates, comprising reacting a silicate with an acid, thus providing a silica gel or suspension, next conducting a first aging step at a pH equal to or above 6 and equal to or less than 8.5, followed by a second aging at a pH equal to or less than 5.0, then separating the silica and washing it with hot water to such extent that an aqueous suspension is produced having a pH, measured on a 20% $SiO_2$ suspension, in accordance with the following equation:

$$pH = d - c \log (D) \qquad \text{(II)}$$

wherein c is a constant equal to or less than 1.0; d is a constant equal to or less than 8.5; and (D) represents the electrical conductivity of the aqueous silica suspension, expressed in microsiemens.cm$^{-1}$ and lastly drying such aqueous suspension.

The present invention also features improved dentifrice compositions comprising the novel silica particulates described in the above embodiments, or prepared by any of the aforesaid process embodiments.

DETAILED DESCRIPTION OF THE PREFERRED EMBODIMENTS OF THE INVENTION

The invention includes several embodiments of novel silica particulates and processes for the production thereof.

Embodiment I

A first embodiment of the present invention features novel silica particulates especially compatible with zinc compounds typically used as dentifrice additives.

More particularly, as indicated above, the essential characterizing features of the subject novel silica particulates reside in the surface chemistry thereof. Thus, surface acidity is an important aspect. Relative to such acidity, one of the distinguishing characteristics of the silica particulates of the invention is the number of their surface acid sites.

This number may be measured as the number of OH or silanol groups per nm$^2$.

Such number is determined as follows:

The number of OH sites on the surface is associated with the amount of water released by silica at temperatures 190° C. and 9000° C.

The silica specimens are initially dried at 105° C. for 2 hours.

A mass Po of silica is placed in a thermobalance and heated to 190° C. for 2 hours; the mass obtained is $P_{190}$. The silica is then heated to 900° C. for 2 hours; the new mass obtained is $P_{900}$.

The number of OH sites is calculated by the following equation:

$$NOH = \frac{66922.2}{A} \times \frac{P_{190} - P_{900}}{P_{190}}$$

wherein NOH is the number of OH sites per nm$^2$ of the surface, and A is the (BET) specific surface of the solid, in m$^2$/g.

In the present embodiment, the silica particulates of the invention advantageously have a number of OH/nm$^2$ less than or equal to 15, more particularly a maximum of 12, and preferably ranging from 3 to 12.

The nature of the OH sites of the silica particulates of the invention, which is also a characteristic of their surface chemistry (pH of the surface), too may be determined by the point of zero charge.

The point of zero charge (PZC) is defined by the pH of a suspension of silica for which the electrical charge of the surface of the solids is zero, regardless of the ionic strength of the medium. This PZC measures the real pH of the face, to the extent that it is free of impurities of the ionic type.

The electrical charge is determined by potentiometry. The principle of the method is based on the total balance of protons adsorbed or desorbed on the surface of the silica at a given pH.

By means of the equations describing the total balance of the operation, it is easy to show that the electrical charge C of the surface, considered relative to a corresponding reference, has a zero surface charge given by the equation:

$$C = \frac{F}{A \cdot M} (H - OH)$$

wherein:

$\underline{A}$ is the specific surface of the solids, in m$^2$/g;

$\underline{M}$ is the mount of solids in the suspension, in g;

$\underline{F}$ is the Faraday constant;

$\underline{H}$ or OH represents the variation per unit of the surface of the excess of H$^+$ or OH$^-$ ions, respectively, of the solids.

The experimental procedure of the determination of PZC is the following:

The method described by Berube and Bruyn, *J. Colloid Interface Sc.*, 27, 305 (1968) is used.

The silica is initially washed in high resistivity deionized water (10 Mega.Ohm.cm), dried and degassed.

In actual practice, a series of solutions at pHo 8.5 is prepared by the addition of KOH or HNO$_3$ and containing an electrolyte (KNO$_3$) in a concentration of from 10$^{-5}$ to 10$^{-1}$ mole/l.

To these solutions, a given mass of silica is added and the pH of the resulting suspensions is permitted to stabilize under agitation, at 25° C. and under nitrogen, for 24 h; its value is the pH'o.

The standard solutions are the supernatants obtained by centrifugation for 30 min at 1,000 rpm of a fraction of the same suspensions; the pH'o is the pH of these supernatants.

The pH of a known volume of these suspensions and of corresponding standard solutions is adjusted to pHo by adding the necessary amount of KOH and the suspensions and standard solutions are permitted to stabilize for 4 hours.

$V_{OH} \cdot N_{OH}$ is the number of equivalents of base added to change from the pH'o to pHo of a known volume (V) of the suspension of the standard solution.

The potentiometric analysis of the suspensions and the standard solutions is carried out from the pHo by the addition of nitric acid to a pHf=2.0.

Preferably, acid is added incrementally corresponding to a variation of the pH by 0.2 pH units. After each addition, the pH is stabilized to attain pHf.

Beginning with pHo, the ($V_H \cdot N_H$ - $V_{OH} \cdot N_{OH}$) is plotted as a function of the pH increments for all of the suspensions (at least 3 ionic strengths) and for all of the corresponding standard solutions.

For each value of pH (no 0.2 unit), the difference between the consumption of H$^+$ or OH$^-$ for the suspension and the corresponding standard solution is then established. This operation is repeated for all ionic strengths.

This gives the (H - OH) corresponding to the consumption of the protons of the surface. The surface charge is calculated by the above equation.

Subsequently, the curves of the surface charge are calculated as a function of the pH for all of the ionic strengths considered. The PZC is defined by the intersection of the curves.

The silica concentration is then adjusted as a function of its specific surface.

For example, 2% suspensions are used for 50 m$^2$/g silica at 3 ionic strengths (0.1, 0.01 and 0.001 mole/l).

100 ml of the suspension are analyzed by using 0.1M potassium hydroxide.

The PZC of the silica particulates of the present invention ranges from 3 to 6.5.

To further improve compatibility, in particular relative to elements other than zinc, in particular fluorine, it is advantageous to limit the aluminum content of the silica of the invention to a maximum of 500 ppm.

The maximum iron content of the silica of the invention should be 200 ppm.

The maximum calcium content may be 500 ppm and more particularly 300 ppm.

The silica of the invention preferably has a maximum carbon content of 50 ppm and more particularly of 10 ppm.

The pH of the silica according to the invention measured by the NFT (French National Standard) standard 45-007 is generally at most 7. More particularly, it ranges from 5.5 to 7, and preferably from 6.0 to 7.0.

These characteristics make it possible to obtain silica particulates that are compatible with zinc compounds. This compatibility, measured by the test described below, is at least 50%, preferably at least 80%, and more preferably at least 90%. Depending upon the particular case, the silica particulates of the invention are also compatible with fluorides, phosphates and derivatives thereof.

In addition to the chemical surface properties described above, which impart compatibility thereto, the silica particulates of the invention have physical properties which are perfectly suited for their use in dentifrices. These structural characteristics are described as follows.

Advantageously, the BET surface of the silica particulates of the invention ranges from 40 to 600 m$^2$/g, and more preferably from 40 to 350 m$^2$/g. Their CTAB surface typically ranges from 4 to 400 m$^2$/g, and more preferably from 40 to 200 m$^2$/g.

The BET surface is determined by the BRUNAUER-EMMET-TELLER method described in the *Journal of the American Chemical Society*, Vol. 60, p. 309 (February 1938) and according to the standard NF X11-622 (3.3).

The CTAB surface is the external surface determined by the ASTM standard D3785, but by using the adsorption of hexadecyltrimethyl ammonium bromide (CTAB) at pH 9 and taking 35 $Å^{02}$ as the projected area of the CTAB molecule.

The silica of the invention may correspond to the three types usually distinguished in the dentifrice field.

Thus, the silica particles of the invention may be of the abrasive type. Same then have a BET surface of from 40 to 300 m$^2$/g. In this case, the CTAB surface ranges from 40 to 100 m$^2$/g.

The silica particles of the invention may also be of the thickening type. Their BET surface then ranges from 120 to 450 m$^2$/g, and more preferably from 120 to 200 m$^2$/g. They may have a CTAB surface of from 120 to 400 m$^2$/g, and more preferably from 120 to 200 m$^2$/g.

Finally, as a third type, the silica particles of the invention may be bifunctional. In this instance they have a BET surface of from 80 to 200 m$^2$/g. Their CTAB surface ranges from 80 to 200 m$^2$/g.

The silica particles of the invention may also exhibit an oil uptake of from 80 to 500 cm$^3$/100 g determined by the NFT standard 30-022 (March 53) using dibutyl phthalate.

More precisely, such oil uptake ranges from 100 to 140 cm$^3$/100 g for the abrasive silica, from 200 to 400 for the thickening silica and from 100 to 300 for the bifunctionals.

The silica particulates preferably have, again vis-a-vis their dentifrice applications, a particle size of from 1 to 10 μm.

This mean particle size is measured by Counter-Coulter.

The apparent density thereof generally ranges from 0.01 to 0.3. In a preferred embodiment of the invention, the silica particulates are precipitated silica particulates.

Finally, the silica of the invention has a refraction index generally from 1.440 to 1.465.

Process for Preparation of Novel Silica Particulates

The process for the preparation of the silica of the invention will now be described in greater detail.

As indicated above, the process is of the type comprising reacting a silicate with an acid, resulting in the formation of a suspension or gel of silica.

It will be appreciated that any known operation may be used to prepare this suspension or gel (addition of acid to the base of a vat of silica, simultaneous total or partial addition of the acid and the silicate to the base of a water vat, or a solution of silicate, etc.), with the selection being made essentially as a function of the physical characteristics of the silica to be produced. It may be advantageous to adjust the pH of the resulting suspension or gel to a value of at most 6 and preferably ranging from 4 to 6.

The silica is then separated from the reaction medium by any known means, for example vacuum filtration or filter press.

A silica filter cake is recovered.

In a primary characteristic of the present embodiment, this filter cake is subjected to a first washing with water, advantageously with deionized water.

The silica particulates are next subjected to a second washing with water, or are treated with an acid solution.

The purpose of the second wash, or acid treatment, is to provide silica particulates having a pH of at most 7, preferably a pH ranging from 5.5 to 7, and more preferably a pH ranging from 6.0 to 7.0, as well as a PZC ranging from 3 to 6.5.

The acid solution may be, for example, a solution of an inorganic acid, such as nitric acid.

However, in a preferred embodiment of the invention, the acid solution may also be a solution of an organic acid, in particular a complexing organic acid. Such an acid is advantageously selected from among carboxylic, dicarboxylic, hydroxycarboxylic and aminocarboxylic acids.

Exemplary of such acids is acetic acid, and exemplary of the complexing acids are tartaric, maleic, glyceric, gluconic and citric acids.

The second wash, or the treatment with acid, may be carried out by pouring the acid solution over the filter cake, or introducing it into the suspension obtained by the comminution or grinding of the cake. Such wash or acid treatment is conducted under conditions as to provide silica particulates having the aforesaid final pH value; the pH of the suspension or medium, prior to drying, must range from 4 to 6, and preferably from 5 to 6.

It may be advantageous, especially in the case in which a solution of a mineral acid is used, to conduct a final wash with deionized water.

In another embodiment of the invention, following the acid/silicate reaction and immediately before the separation of the silica, the suspension or gel is aged. This aging is typically carried out at a maximum pH of 6, for example, at a value of from 4 to 6.

It is also possible to carry out the aging during the reaction, for example at a pH of from 6 to 8. The aging is preferably conducted at an elevated temperature, for example a temperature of from 80° to 100° C., and for a period of time ranging from fifteen minutes to two hours.

After the cake is washed and treated as described above, the cake, or if it is comminuted, the suspension is dried by any known means. In particular, drying is by atomization. The dried product is ground, if necessary, to obtain the grain size distribution desired.

Improved Dentifrice Compositions

This invention also features improved dentifrice compositions containing the above novel silica particulates, advantageously prepared by the aforesaid distinct processes.

The amount of silica incorporated into such improved dentifrice compositions may vary over wide limits, but typically it ranges from 5 to 35% by weight.

The silica particulates of the invention are well adapted for incorporation into dentifrice compositions comprising at least one element selected from among the fluorides, phosphates, and zinc.

As regards the fluoride compounds, the amount thereof preferably corresponds to a fluorine concentration in the ultimate composition of from 0.01 to 1% by weight, notably from 0.1 to 0.5% by weight. The preferred fluoride compounds are the salts of monofluorophosphoric acid, and in particular those of sodium, potassium, lithium, calcium, aluminum and ammonium, mono- and difluorophosphate, as well as the various fluorides containing fluorine in the form of a bonded ion, particularly alkaline fluorides, such as those of sodium, potassium, lithium, ammonium fluoride, stannous fluoride, manganese fluoride, zirconium fluoride, aluminum fluoride, together with addition products of these fluorides with each other or with other fluorides, such as potassium, sodium or manganese fluorides.

Other fluorides may also be incorporated in the dentifrices of the present invention, such as, for example, zinc fluoride, germanium fluoride, palladium and titanium fluorides, and alkaline fluozirconates, such as, for example, of sodium or potassium, stannous fluozirconate, and sodium or potassium fluoborate or fluosulfates.

Organic fluorine compounds may also be incorporated, preferably known compounds such as the addition products of amines and long chain aminoacids with hydrogen fluoride, cetylamine fluoride, the dihydrofluoride or bis(hydroxyethyl)aminopropyl-N-hydroxyethyl octadecylamine, octadecylamine fluoride and the dihydrofluoride of N,N', N'tri-(polyoxyethylene)-N-hexadecylpropylenediamine.

Zinc is incorporated, in particular, in the form of its citrate or sulfate.

As elements that are useful as anti-plaque agents of the polyphosphate or polyphosphonate, guanidine, or bisbiguanide type, those set forth in U.S. Pat. Nos. 3,934,002 and 4,110,083 are representative.

The subject dentifrice compositions may also comprise a binder.

The principal binders are selected from among:

(i) Cellulose derivatives: methylcellulose, hydroxyethyl cellulose, sodium carboxymethylcellulose;

(ii) Mucilages: carraghenates, alginates, agar-agar and geloses;

(iii) Gums: arabic and tragacanth gums, xanthan gum, Karaya gum;

(iv) Carboxyvinyl and acrylic polymers;

(v) Polyoxyethylene resins.

In addition to the silica particulates of the invention, the dentifrice compositions may contain one or more other abrasive polishing agents selected from among:

(i) Precipitated calcium carbonate;

(ii) Magnesium carbonate;

(iii) Di- and tricalcium phosphates;

(iv) Insoluble sodium metaphosphate;

(v) Calcium pyrophosphate;

(vi) Titanium dioxide (whitening agent);

(vii) Silicates;

(viii) Alumina and silicoaluminates;

(ix) Zinc and tin oxides;

(x) Talc;

(xi) Kaolin.

These dentifrice compositions may also contain detergents, humectants, aromatics, sweeteners and colorants and preservatives.

The principal detergents are selected from among:

(i) Sodium laurylsulfate;

Sodium laurylether sulfate and laurylsulfoacetate;

(iii) Sodium dioctylsulfosuccinate;

(iv) Sodium laurylsarcosinate;

(v) Sodium ricinoleate;

(vi) Monoglycerine sulfates.

The principal humectants are selected from among the polyalcohols, such as:

(i) Glycerol;

(ii) Sorbitol, generally in a 70% solution in water;

(iii) Propylene glycol.

The principal aromatics are selected from among: essences of anise, chinese anise, mint, juniper berry, cinnamon, cloves and roses.

The principal sweetening agents are orthosulfobenzoic imides and cyclamates.

The principal colorants are those selected from among:

(i) Red and rose colorants: amaranth, azorubin, catechou, new coccine (PONCEAU 4 R), cochineal, erythrosine;

(ii) Green colorants: chlorophyll and chlorphylline;

(iii) Yellow colorants: sun yellow (Orange S) and quinoline-yellow.

The principal preservatives are: parahydroxy benzoates, formaldehyde and products releasing same, hexetidine, quaternary ammonium compounds, hexachlorophene, bromophene and hexamedine.

Finally, the dentifrice compositions may contain therapeutic agents, principally selected from among:

(i) Antiseptics and antibiotics;

(ii) Enzymes;

(iii) oligoelements and the fluorine compounds described above.

Illustrative Examples

In order to further illustrate the present invention and the advantages thereof, the following specific examples are given, it being understood that same are intended only as illustrative and in nowise limitative.

In said examples to follow, the tests described immediately below were carried out to measure the compatibility of the silica with various compounds.

$$\% \text{ Compatibility} = \frac{\text{absorbance of test solution}}{\text{absorbance of reference solution}} \times 100$$

Measurement of compatibility with fluorides;

4 g silica were dispersed in 16 g of a 0.3% solution of sodium fluoride (NaF). The suspension was agitated for 24 h at 37° C. After centrifugation at 20,000 rpm for 30 min, the supernatant was filtered on a 0.2 μm Millipore filter. The solution obtained in this manner constituted the test solution.

A reference solution was prepared by the same procedure, but without the silica.

The compatibility with fluorides was determined by the % of free fluoride measured by a fluoride selective electrode (Orion).

It was determined by the following relationship:

$$\% \text{ Compatibility} = \frac{\text{Concentration in F of the test solution}}{\text{Concentration in F of the reference solution}} \times 100$$

Measurement of compatibility with zinc:

4 g silica were dispersed in 100 ml of a 0.06% aqueous solution of $ZnSO_4 \cdot 7 H_2O$. A suspension was obtained, the pH of which was stabilized at 7 in 15 min by the addition of NaOH or $H_2SO_4$. The suspension was then agitated for 24 h at 37° C. and centrifuged at 20,000 rpm for 30 min.

The supernatant, filtered on a 0.2 μm Millipore filter, constituted the test solution.

A reference solution was prepared by the same procedure, but without the silica.

The concentration of free zinc in the two solutions was determined by atomic absorption (214 nm).

The compatibility was determined by the following relationship:

$$\% \text{ Compatibility} = \frac{\text{Concentration of Zn in the test solution}}{\text{Concentration of Zn in the reference solution}} \times 100$$

Measurement of compatibility with sodium and potassium pyrophosphates:

4 g silica were dispersed in 16 g of a 1.5% aqueous suspension of sodium or potassium pyrophosphate. The suspension was agitated for 24 h at 37° C., then centrifuged at 20,000 rpm for 30 min.

The supernatant was filtered on a 0.2 μm Millipore filter. 0.2 g of the solution, diluted in 100 ml water in a volumetric flask, constituted the test solution.

A reference solution was prepared by the same procedure, but without the silica.

The free pyrophosphate ion ($P_2O_7^=$) concentration of the two solutions was determined by ionic chromatography (DIONEX 2000i system), equipped with an integrator.

The compatibility was determined from the areas of the peaks obtained in the chromatograms and corresponding to the retention time of the pyrophosphate in the test and reference solutions.

$$\% \text{ Compatibility} = \frac{\text{Area of the peak of the test solution}}{\text{Area of the peak of the reference solution}} \times 100$$

EXAMPLE 1

Into a reactor equipped with a temperature and pH control system and a turbine agitation system, 6 l of deionized water were introduced.

After commencing agitation (300 rpm), the contents of the reactor were heated to 85° C.

When this temperature was reached, the following materials were simultaneously added: 8.5 l sodium silicate having a silica concentration of 120 g/l and a $SiO_2/Na_2O$ ratio of 3.5, at a flow rate of 0.34 l/min, and 13.5 l sulfuric acid having a concentration of 80 g/l. The acid flow rate was adjusted such that the pH of the medium was maintained at a constant value 8.0.

After 40 min of addition, the mixture was aged for 10 min at this pH and temperature.

The addition of the silicate was discontinued and the addition of the acid continued until the pH of the reaction mixture was stabilized at 4.

The mixture was then aged for 15 min at this pH and at 85° C.

It was subsequently filtered and the moist filter cake was washed with deionized water.

The filter cake was then dispersed in deionized water to form a homogeneous suspension having a silica concentration of 50 g/l. The pH of this suspension was adjusted to 5.8 by the addition of nitric acid and it was permitted to stabilize at this pH for 15 min.

The suspension was filtered.

The product was then dried by atomization and ground in a forplex type grinder to produce a grain size of 9 microns.

The physico/chemical properties of the resulting silica particulates were as follows:

| | | |
|---|---|---|
| (i) BET surface | 90 $m^2/g$ | |
| (ii) CTAB surface | 60 $m^2/g$ | |
| (iii) Oil uptake | 105 $cm^3/100$ g | |
| (iv) pH | 6.8 | |
| (v) Number of $OH/nm^2$ | 8. | |

The chemical analyses of the silica are reported in the following table:

| Ions | Al | Fe | Ca | C |
|---|---|---|---|---|
| ppm | 350 | 110 | 300 | 10 |

The PZC of the silica was 4.5.

In the following table the different compatibilities of the silica particles with the various ingredients of a dentifrice formulation and measured by the different tests described above, are set forth:

| Ingredients | Fluoride (NaF) | Pyrophosphate (Na/K) | Zinc ($ZnSO_4$) |
|---|---|---|---|
| % Compatibility | 90 | 98 | 90 |

COMPARATIVE EXAMPLE 2

As a comparison, compatibility measurements were made using the commercial silica typically employed in dentifrice formulations, and these are reported below, together with the physico/chemical properties thereof:

| Silica (trademark of manu-facturer) | Surfaces ($m^2/g$) | | Number | Compatibilities | | |
|---|---|---|---|---|---|---|
| | CTAB | BET | $OH/nm^2$ | Zn | F | Pyrophosphate |
| Zeodent (Hubert) | 50 | 100 | 30 | 0 | 95 | 95 |
| Tixosil 53 (Rhone-Poulenc) | 50 | 250 | 30 | 0 | 60 | 90 |
| Z 119 (Rhone-Poulenc) | 50 | 60 | 25 | 20 | 95 | 95 |

It should be noted that for the silica of this table the PZC was less than 3.

EXAMPLE 3

This example relates to the formulation of an opaque dentifrice of the paste type:

Its formula was the following:

| | |
|---|---|
| Glycerin | 22.00 |
| CMC 7mFD | 1.00 |
| Sodium saccharinate | 0.20 |
| Sodium monofluorophosphate | 0.76 |
| Sodium fluoride | 0.10 |
| Sodium lauryl sulfate (30% aqueous) | 4.67 |
| Sodium benzoate | 0.10 |
| Perfume | 0.90 |
| Titanium dioxide | 1.00 |
| Silica of Example 1 | 31.50 |
| $ZnSO_4.7H_2O$ | 0.48 |
| Distilled water | 37.29 |

Rheological testing and visual examination of the above paste dentifrice evidenced that the conventional properties thereof were good.

Embodiment II

According to a second embodiment of the present invention, the silica particulates have improved compatibility with guanidine and surface acidity is an important aspect. Relative to surface acidity, one of the distinguishing characteristics of the silica particulates of the invention is the strength of their surface acid sites.

By the term "acidity" is intended acidity in the sense of a Lewis acid, i.e., connoting the tendency of one site to accept a pair of electrons from a base according to the equilibrium:

$$B: + A = BA$$

In characterizing the silica particulates of the invention, the convention of "acidity function", Ho, developed by Hammett, is used to measure the tendency of the acid, silica in this case, to accept a pair of electrons from base.

The Ho function is defined by the conventional relationship:

$$pK_a + \log \frac{(B:)}{(B:)(A)} = Ho$$

To determine the strength of the acid sites of a silica of the invention by the Hammett method, the indicator technique is used, described originally by Wailing, *J. Am. Chem. Soc.*, 72, 1164 (1950).

The strength of the acid sites is determined by colored indicators, and the $pK_a$ of transfer between the acid and basic states under the conditions of use, which are known.

Thus, the lower the $pK_a$ of the indicator undergoing the change in color, the stronger the acidity of the site. The following table compiles, for exemplary purposes, a non-limiting list of Hammett indicators suitable for use in circumscribing the value of Ho, by determining in which form two successive indicators are adsorbed.

TABLE I

| | Color | | |
|---|---|---|---|
| Indicator | Basic Form | Acid Form | $pK_a$ |
| Neutral red | yellow | red | +6.8 |
| Methyl red | yellow | red | +4.8 |
| Phenylazonaphthylamine | yellow | red | +4.0 |
| p-Dimethylaminoazobenzene | yellow | red | +3.3 |
| 2-Amino-5-azotoluene | yellow | red | +2.0 |
| Benzene azodiphenylamine | yellow | red | +1.5 |
| 4-Dimethylaminozao-1-naphthalene | yellow | red | +1.2 |

TABLE I-continued

| | Color | | |
|---|---|---|---|
| Indicator | Basic Form | Acid Form | $pK_a$ |
| Crystal violet | blue | yellow | +0.8 |
| p-Nitrobenzene azo-(p'-nitro) diphenylamine | orange | violet | +0.43 |
| Dicinnamalacetone | yellow | red | −3.0 |
| Benzalacetophenone | colorless | yellow | −5.6 |
| Anthraquinone | colorless | yellow | −8.2 |

The color of the indicators adsorbed onto the silica is a measure of the strength of the acid sites. If the color is that of the acid form of the indicator, the value of the Ho function of the surface is equal to or less than the $pK_a$ of the indicator.

Low values of Ho correspond to high strengths of the acid sites.

Thus, for example, a silica giving a red color with p-dimethylaminoazobenzene and yellow with 2-amino-5-azotoluene would have an acid function Ho ranging from 3.3 to 2.

Experimentally, the determination is carried out with 0.2 g silica placed in a test tube in the presence of an indicator solution, in a concentration of 100 rag/l in cyclohexane.

The silica is initially dried at 190° for 2 hours and maintained, to the exclusion of humidity, in a desiccator.

By means of agitation, the adsorption if it takes place, is produced in a few minutes and the change in color is visible to the naked eye or may optionally be observed by studying the characteristic absorption spectra of the color indicators adsorbed, both in their acid and their basic forms.

A first characteristic of the silica particulates of the invention is that they have an acidity function, determined as described above, of at least 3.3.

The strength and the nature of the surface acid sites may also be measured by the infrared spectrometry of pyridine adsorbed onto the silica.

It is known that the amount of pyridine adsorbed onto a solid mass makes it possible to determine, in particular, the nature of the surface acid sites.

Pyridine is a relatively strong base ($pK_b$=5).

The formation of the pyridinium ion (PyH+) further permits differentiation of sites of the Lewis and Bronsted type.

Information concerning the acidity of a surface of a solid may also be obtained by studying the absorption bands of pyridine in the range of 1,700 $cm^{-1}$ to 1,400 $cm^{-1}$.

Furthermore, the value of the deviation of the characteristic bands of pyridine and its ionized forms, before and after adsorption, makes it possible to quantify the strength of the acid sites.

The pyridinium ion gives a band at 1,540 $cm^{-1}$, while pyridine bonded by H bonds or by coordination, gives a band in the range of 1,400–1,465 $cm^{-1}$. It also appears that the pyridine band located at 1,583 $cm^{-1}$ is displaced, if the pyridine is adsorbed. This band indicates the presence of Lewis acid sites. The acid strength of the latter is proportional to the displacement of the band.

In summary, it is possible to use the bands of 1,540, 1,650 and 1,485 $cm^{-1}$ to define acidity of the Bronsted type, and the range of 1,440–1,465 $cm^{-1}$ for Lewis acidity.

Experimentally, the measurements are carried out using a silica suspension in carbon tetrachloride, in the presence of pyridine.

The silica is first dried at 190° C. for 2 hours, and maintained with the exclusion of humidity. After cooling, 1 g silica is dispersed by magnetic agitation followed by ultrasonic dispersion (10 min) in 50 ml $CCl_4$.

0.8 mg pyridine is added per square meter of the silica introduced. The dispersion is heated at reflux, under agitation, for 1 hour.

The same procedure is used to prepare a control solution of the same pyridine concentration, but without silica, and a control solution of the same silica concentration, but without pyridine.

The adsorption spectra of pyridine is determined by infrared spectroscopy of the suspension, the solution of pyridine without silica and the silica suspension without pyridine.

From the spectra obtained from the suspension, the spectra corresponding to the control solution and the spectra corresponding to the control suspension, are subtracted.

The silica is characterized by the position of the remaining bands and the displacement of the pyridine and pyridium ion absorption bands relative to the position of the bands of their unadsorbed forms.

In general, the spectra obtained should not display the pyridinium peak (band at 1,540 $cm^{-1}$), the absence of the peak indicating that the silica has an acid function Ho of at least 3.3.

The magnitude of the displacement of the pyridine and pyridine adsorbed makes it possible to determine the Acidity of the surface acid sites. Typically, for the band of 1,440 $cm^{-1}$ this displacement ($\Delta v$) should be at most 10 $cm^{-1}$, more particularly 5 $cm^{-1}$ at most.

In a preferred embodiment of the invention, this $\Delta v$ is zero.

The silica described above displays good compatibility with chlorhexidine; this compatibility, measured by the test described above, should be at least 65%, in particular at least 80% and preferably at least 90%.

However, in another preferred embodiment of the invention, the silica is also compatible with fluorine values. In this case, there is a maximum content of anions of the type of $SO_4^{2-}$, $Cl^-$, $NO_3^-$, $PO_4^{3-}$, $CO^{2-}$, of $5 \times 10^{-3}$ moles per 100 g silica.

This compatibility becomes greater with declining values of such content. Preferably, it will be a maximum of $1 \times 10^{-3}$ moles and more preferably $0.2 \times 10^{-3}$ per 100 g silica.

In the case of silica prepared from sulfuric acid, this anion content is more conveniently expressed as content in $SO_4$, by weight. In this case, the maximum content is 0.5%.

In another preferred embodiment of the invention, such maximum content is 0.1% and more preferably 0.02%.

Such compatibility may be improved further, in particular relative to certain elements such as zinc, by observing the conditions of the number of acid sites of the surface. This number may be measured as the number of OH or silanol groups per $nm^2$, and is determined as described above in Embodiment I.

In the present embodiment, the silica particulates advantageously have a number of $OH/nm^2$ less than or equal to 15, more particularly a maximum of 12, and preferably ranging from 3 to 12.

The nature of the OH sites of the silica particulates, which is also characteristic of their surface chemistry, may also be determined by the point of zero charge (PZC). The method for determining the PZC is as described in Embodiment I.

In actual practice, it is preferable that the value of said PZC be at least 3 and more particularly from 4 to 6. In the case of better compatibility with zinc, it is 6.5 at maximum. For fluorine compatibility, a maximum PZC of 7 is preferred.

To further improve compatibility, in particular relative to fluorine, it is advantageous to limit the aluminum content of the silica of the invention to a maximum of 500 ppm.

The maximum iron content of the silica of the invention should be 200 ppm.

The maximum calcium content may be 500 ppm and more particularly 300 ppm.

The silica of the invention preferably has a maximum carbon content of 50 ppm and more particularly of 10 ppm.

The pH of the silica according to the invention measured by the NFT (French National Standard) standard 45-007 is generally at most 8. More particularly, it ranges from 6.0 to 7.5.

These characteristics make it possible to obtain silica particulates that are compatible with at least the guanidines and in particular chlorhexidine, and, depending upon the particular case, also with fluorides, phosphates and their derivatives and particularly zinc.

Advantageously, the BET surface of the silica particulates of the invention ranges from 40 to 600 $m^2/g$, and more preferably from 40 to 350 $m^2/g$. Their CTAB surface typically ranges from 4 to 400 $m^2/g$, and more preferably from 40 to 200 $m^2/g$.

In addition to the chemical surface properties described above, which impart compatibility thereto, the silica particulates of the invention have physical properties which are perfectly suited for their use in dentifrices. These structural characteristics are described as follows.

The BET surface is determined by the BRUNAUER-EMMET-TELLER method described in the *Journal of the American Chemical Society*, Vol. 60, p. 309 (February 1938) and according to the standard NF X11-622 (3.3).

The CTAB surface is the external surface determined by the ASTM standard D3785, but by using the adsorption of hexadecyltrimethyl ammonium bromide (CTAB) at pH 9 and taking 35 $Å^2$ as the projected area of the CTAB molecule.

The silica of the invention may correspond to the three types usually distinguished in the dentifrice field.

Thus, the silica particles of the invention may be of the abrasive type. Same then have a BET surface of from 40 to 300 $m^2/g$. In this case, the CTAB surface ranges from 40 to 100 $m^2/g$.

The silica particles of the invention may also be of the thickening type. Their BET surface then ranges from 120 to 450 $m^2/g$, and more preferably from 120 to 200 $m^2/g$. They may have a CTAB surface of from 120 to 400 $m^2/g$, and more preferably from 120 to 200 $m^2/g$.

Finally, as a third type, the silica particles of the invention may be bifunctional. In this instance they have a BET surface of from 80 to 200 $m^2/g$. Their CTAB surface ranges from 80 to 200 $m^2/g$.

The silica particles of the invention may also exhibit an oil uptake of from 80 to 500 $cm^3/100$ g determined by the NFT standard 30-022 (March 53) using dibutyl phthalate.

More precisely, such oil uptake ranges from 100 to 140 $cm^3/100$ g for the abrasive silica, from 200 to 400 for the thickening silica and from 100 to 300 for the bifunctionals.

The silica particulates preferably have, again vis-a-vis their dentifrice applications, a particle size of from 1 to 10 μm.

This mean particle size is measured by Counter-Coulter.

The apparent density thereof generally ranges from 0.01 to 0.3. In a preferred embodiment of the invention, the silica particulates are precipitated silica particulates.

Finally, the silica of the invention has a refraction index generally from 1.440 to 1.465.

Process for Preparation of Novel Silica Particulates

The process for the preparation of the silica of this embodiment of the invention will now be described in greater detail.

As indicated above, the process is of the type comprising reacting a silicate with an acid, resulting in the formation of a suspension or gel of silica.

It will be appreciated that any known operation may be used to prepare this suspension or gel (addition of acid to the base of a vat of silica, simultaneous total or partial addition of the acid and the silicate to the base of a water vat, or a solution of silicate, etc.), with the selection being made essentially as a function of the physical characteristics of the silica to be produced. It may be advantageous to adjust the pH of the resulting suspension or gel to a value of at most 6 and preferably ranging from 4 to 6.

The silica is then separated from the reaction medium by any known means, for example vacuum filtration or filter press.

A silica filter cake is recovered.

The process of the invention may then be carried according to two principal variants.

The first variant features the preparation of silica particulates essentially completely compatible with the guanidines and specifically with chlorhexidine.

In this case, the process includes a washing of the filter cake. Washing is with water, generally deionized water, until a wash filtrate having a conductivity of less than 200 microsiemens.cm$^{-1}$ ($\mu$S/cm) is obtained.

If it is desired to further improve the compatibilities of the silica obtained by such process, the washing is continued to a greater extent.

In particular, in a preferred embodiment of the invention, the washing is continued until a conductivity of the water of maximum 100 microsiemens.cm$^{-1}$ is obtained.

After the cake is washed as described above, the cake, or if it is comminuted, the suspension, is dried by any known means. In particular, drying is by atomization. The dried product is ground, if necessary, to obtain the grain size distribution desired.

The second variant of the process features the preparation of silica particulates compatible with other elements, such as fluorine, zinc and phosphates, in addition to the guanidines.

In this variant, the process again includes washing with deionized water, as in the first variant. However, this washing may be less extensive. It may be continued, for example, until a filtrate having a conductivity of maximum 2,000 microsiemens.cm$^{-1}$ is obtained.

In this second variant, following the first washing operation, a second washing, or a treatment of the filter cake with an acid solution or acidulated water, is carried out. This second washing or treatment is carried out such that a silica is produced having a maximum pH of 8, preferably ranging from 6.0 to 7.5, and a PZC of at least 3, and preferably from 4 to 6.

This washing or treatment may be carried out by pouring the acid solution over the filter cake, or introducing it into the suspension obtained by the comminution of the cake.

The acid washing or treatment is carried out under conditions such that, in order to produce a silica having the pH values indicated above, the pH of the suspension or medium prior to drying must range from 4 to 8, in particular from 5 to 8 and preferably from 6 to 7.

This acid solution may be, for example, a solution of an inorganic acid, such as nitric acid.

However, in another preferred embodiment of the invention, the acid solution may also be a solution of an organic acid, in particular a complexing organic acid. Such acid is advantageously selected from among carboxylic, dicarboxylic, hydroxycarboxylic and aminocarboxylic acids.

Exemplary of such acids is acetic acid, and exemplary of the complexing acids are tartaric, maleic, glyceric, gluconic and citric acids.

It may be advantageous, especially in the case in which a solution of a mineral acid is used, to conduct a final wash with deionized water.

Following the washes or treatments according to the second variant, drying is carried out in the manner described for the first variant.

In another embodiment of the invention, following the acid/silicate reaction and immediately before the separation of the silica, the suspension or gel is aged. This aging is typically carried out at a maximum pH of 6, for example, at a value of from 4 to 6.

It is also possible to carry out the aging during the reaction, for example at a pH of from 6 to 8. The aging is preferably conducted at an elevated temperature, for example a temperature of from 80° to 100° C., and for a period of time ranging from fifteen minutes to two hours.

Finally, it has been observed that it is possible to further improve the compatibility of the silica of the invention by another supplemental treatment.

This treatment entails the use of an alkaline earth metal. This element may be introduced either into the suspension or gel of the silica, or, preferably, into the filter cake, in particular after the comminution thereof, in the form of a salt or hydroxide, for example.

More particularly, a complexing organic salt of an alkaline earth metal, typically a barium salt, for example a barium acetate, is used.

Improved Dentifrice Compositions

This embodiment of the invention also features improved dentifrice compositions containing the above novel silica particulates, advantageously prepared by the aforesaid distinct processes.

The silica particulates of the invention are well adapted for incorporation into dentifrice compositions comprising at least one element selected from among the fluorides, phosphates, guanidines, and especially chlorhexidine. The silica particulates advantageously displays a compatibility, according to the tests described hereinafter, of at least 90% for each of these elements.

The silica particulates of the invention are also compatible with maleic acid/vinylethylether copolymers and may be incorporated in dentifrice compositions containing these copolymers. Finally, they advantageously have a compatibility with zinc of at least 50% and preferably at least 80%.

The composition of the improved dentifrice incorporating the novel silica particulates is as described above in Embodiment I.

Illustrative Examples

In order to further illustrate the present invention and the advantages thereof, the following specific examples are given, it being understood that same are intended only as illustrative and in nowise limitative.

Measurement of compatibility with chlorhexidine:

4 g silica were dispersed in 16 g of a 1% aqueous solution of chlorhexidine digluconate.

The suspension was agitated for 24 h at 37° C.

The suspension was then centrifuged at 20,000 rpm or 30 min and the supernatant was filtered on a 0.2 $\mu$m Millipore filter.

0.5 ml of the filtered solution was withdrawn and diluted in 100 ml water in a volumetric flask. This solution constituted the test solution.

A reference solution was prepared by the same procedure, but without the silica. A 1% aqueous solution of chlorhexidine digluconate was agitated for 24 h at 37° C., then centrifuged at 20,000 rpm and the supernatant filtered on a 2 μm Millipore filter. 0.5 ml of the resulting solution is diluted in 100 ml water in a volumetric flask.

The absorbance of the two solutions was then measured at 254 nm by means of a spectrophotometer (Uvicon 810/830).

The amount of free chlorhexidine, designated the % Compatibility, was determined by the relationship:

$$\% \text{ Compatibility} = \frac{\text{absorbance of test solution}}{\text{absorbance of reference solution}} \times 100$$

The measurement of the compatibility of the silica particulates with other dentifrice components (fluorides, zinc and sodium and potassium pyrophosphates) was carried out as described in Embodiment I.

In said examples to follow, the tests described immediately below were carried out to measure the compatibility of the silica with various compounds.

EXAMPLE 4

This example relates to the preparation of a compatible silica of the abrasive type.

Into a reactor equipped with a temperature and pH control system and a turbine agitation system, 6 l of deionized water were introduced.

After commencing agitation, the contents of the reactor were heated to 85° C.

When this temperature was reached, the following materials were simultaneously added: 8.5 l sodium silicate having a silica concentration of 120 g/l and a $SiO_2/NaO$ ratio 3.5, at a flow rate of 0.34 l/min, and 13.5 l sulfuric acid having a concentration of 80 g/l. The acid flow rate was adjusted such that the pH of the medium was maintained at constant value of 8.0.

After 40 min of addition, the addition of the silicate was discontinued and the addition of the acid continued until the pH of the reaction mixture was stabilized at 4.

The mixture was then aged for 15 min at this pH and at 85 ° C.

The mixture was then filtered and the moist filter cake was washed with deionized water until the conductivity of the filtrate was less than 100 μS/cm.

The filter cake was then washed with water adjusted to pH 4 by the addition of acetic acid.

A final wash was carried out with deionized water.

The product was then dried by atomization and ground in a forplex type grinder to produce a grain size of 10 microns.

The physico/chemical properties of the resulting silica particulates were as follows:

| | | |
|---|---|---|
| (i) BET surface | 100 m²/g |
| (ii) CTAB surface | 55 m²/g |
| (iii) oil uptake | 120 cm³/100 g |
| (iv) pH | 6.5 |

The chemical analyses of the silica are reported in the following table:

| Ions | SO₄ | Al | Fe | Ca | C |
|---|---|---|---|---|---|
| ppm | 100 | 250 | 130 | 300 | 10 |

The surface chemistry was quantified by the following parameters:

Ho higher than 3.3

PZC=4

$\Delta v = 5$ cm$^{-1}$

Number of OH/nm²=9.

The following table sets forth the compatibilities the silica particles with the various ingredients of a dentifrice composition.

| Ingredients | Fluoride (NaF) | Pyrophosphate (Na/K) | Chlorhexidine (digluconate) | Zinc (ZnSO₄) |
|---|---|---|---|---|
| % Compatibility | 95 | 98 | 75 | 70 |

EXAMPLE 5

The procedure of Example 4 was repeated to obtain a silica filter cake which was washed with water having a pH of 4, by addition of acetic acid thereto.

The cake obtained in this manner was comminuted such as to provide a fluid suspension.

0.2 g barium acetate was added under agitation.

The silica was then dried by atomization and ground to produce a mean particle size of 10 μm.

The physico/chemical properties of the resulting silica particles were the following:

| | | |
|---|---|---|
| (i) BET surface | 100 m²/g |
| (ii) CTAB surface | 60 m²/g |
| (iii) oil uptake | 110 cm³/100 g |
| (iv) pH | 6.5 |

The chemical analyses of the silica are reported in the following table:

| Ions | SO₄ | Al | Fe | Ca | C |
|---|---|---|---|---|---|
| ppm | 100 | 250 | 130 | 300 | 10 |

The surface chemistry was quantified by the following parameters:

Ho higher than 3.3

PZC=4.5

$\Delta v = 2$ cm$^{-1}$

Number of OH/nm²=8

| Ingredients | Fluoride (NaF) | Pyrophosphate (Na/K) | Chlorhexidine (digluconate) | Zinc (ZnSO₄) |
|---|---|---|---|---|
| % Compatibility | 95 | 98 | 90 | 70 |

EXAMPLE 6

This example relates to the preparation of a silica gel thickener.

Into a reactor equipped with a temperature and pH control system and a turbine agitation system, 14 l Na silicate were introduced, having a silica concentration of 86 g/l and a $SiO_2/Na_2O$ ratio of 3.5.

After commencing agitation (100 rpm), 1.45 l of 28% ammonia were added over 2 min.

0.8 l sulfuric acid having a concentration of 200 g/l was then introduced, at a flow ram of 0.2 l/min.

The mixture was then reacted for 5 min at a temperature of 20° C.

5.2 l sulfuric acid having a concentration of 200 g/l were then added, at a rate of 0.2 l/min.

Following the appearance of the gel (visual or by measuring the turbidity), the mixture was aged for 10 min.

The gel was dispersed by agitating the mixture at 400 rpm for 30 min.

The pH of the medium was then reduced to a value of 3.5 by the addition of sulfuric acid (200 g/l) at a rate of 0.2 l/min.

The reaction mixture was permitted to stabilize for 1 h at 60° C.

The gel was prepared by filtering this mixture and washing the resulting filter cake twice with 20 l deionized water at 60° C. and with 20 l water at pH 3.

The treatment according to the present embodiment was then carried out by washing with deionized water at 20° C. until a seductivity of 200 microsiemens.cm$^{-1}$ was obtained.

The resulting cake was comminuted to form a homogeneous suspension of silica in a concentration of 10%, adjusted by the addition of water.

The silica was dried by atomization using an Anhydro type atomizer. The silica was then micronized in a JET Pulverizer grinder to produce a grain size of 1.5 μm.

The physico/chemical properties of the resulting silica particles were as follows:

|  |  |  |
|---|---|---|
| (i) BET surface | 450 m$^2$/g |
| (ii) CTAB surface | 350 m$^2$/g |
| (iii) oil uptake | 300 cm$^3$/100 g |
| (iv) pH | 6.8 |
| (v) Apparent density | 0.270 |
| (vi) Refractive index | 1.445 |

The chemical analyses of the resulting silica particles are reported in the following table:

| Ions | SO$_4$ | Al | Fe | Ca | C |
|---|---|---|---|---|---|
| ppm | 500 | 200 | 120 | 300 | 10 |

The surface chemistry was quantified by the following parameters:

Ho higher than 3.3
PZC=3.6
No pyridine adsorption bands.

Compatibilities:

| In-gredients | Fluoride (NaF) | Pyrophosphate (Na/K) | Chlorhexidine (digluconate) | Zinc (ZnSO$_4$) |
|---|---|---|---|---|
| % Compatibility | 90 | 95 | 65 | 50 |

EXAMPLE 7

This example relates to the production of a silica thickening agent.

Into a reactor equipped with a pH and temperature control system, 6 l water were introduced and subsequently, under agitation, 150 g sodium sulfate were added thereto.

The mixture was heated to 60° C. and, simultaneously, 10 l sodium silicate (Rm=3.5 and $SiO_2$=220 g/l) and sulfuric acid having a concentration of 80 g/l, were added over 40 min.

The flow rate of the sulfuric acid was adjusted such as to maintain the pH of the reaction medium at a constant 7.8.

The pH of the medium was stabilized at 4.0 by the very rapid addition of sulfuric acid. It was permitted to age for 15 min at 60° C.

The reaction mixture was filtered at 60° C. and the silica filter cake was washed with deionized water such as to provide a conductivity of the filtrate of 900 microsiemens.cm$^{-1}$. The cake was then washed with water at pH 4, adjusted by the addition of acetic acid and a final wash was carried out with deionized water.

The silica cake obtained in this manner was comminuted and, under agitation, 2 g calcium acetate were added thereto.

The silica was dried by atomization and micronized by a JET pulverizer to adjust the particle size to 1.5 μm.

The physico/chemical properties of the resulting silica particles were as follows:

|  |  |  |
|---|---|---|
| (i) BET surface | 320 m$^2$/g |
| (ii) CTAB surface | 120 m$^2$/g |
| (iii) oil uptake | 250 cm$^3$/100 g |
| (iv) pH | 6.5 |

The chemical analyses of the resulting silica particles are reported in the following table:

| Ions | SO$_4$ | Al | Fe | Ca | C |
|---|---|---|---|---|---|
| ppm | 100 | 200 | 120 | 300 | 20 |

The surface chemistry was quantified by the following parameters:

Ho higher than 3.3
PZC=4.0
Number of OH/nm$^2$=11
No pyridine adsorption bands

| In-gredients | Fluoride (NaF) | Pyrophosphate (Na/K) | Chlorhexidine (digluconate) | Zinc (ZnSO$_4$) |
|---|---|---|---|---|
| % Compatibility | 90 | 95 | 90 | 80 |

EXAMPLE 8

This example relates to the preparation of abrasive silica particulates.

Into a reactor equipped with a temperature and pH control system and a turbine agitation system, 6 l deionized water were introduced.

After commencing agitation (300 rpm), the contents of the reactor were heated to 85° C.

When this temperature was attained, 8.5 l sodium silicate having a concentration in silica of 120 g/l, an $SiO_2/Na_2O$ ratio of 3.5 and a flow rate of 0.34 l/min, and 13.5 l sulfuric acid having a concentration of 80 g/l, were simultaneously added. The flow rate of the acid was adjusted such that the pH of the medium was maintained at a constant 8.0.

After 40 min of addition, the addition of silicate was discontinued and the mixture was aged for 15 min at 85° C. and pH 8.

The addition of the acid was continued until the pH of the mixture was stabilized at 4.

The mixture was then aged for 15 min at this pH and at 85° C.

The mixture was then filtered and the moist filter cake washed with deionized water until the conductivity of the filtrate was 100 microsiemens.cm$^{-1}$.

Two washes were then carried out with water adjusted to pH 4, by addition of acetic acid thereto.

A final wash was conducted with deionized water.

The product was then dried by atomization and ground to a gain size of 9.0 microns in a forplex type grinder.

The physico/chemical properties of the resulting silica particles were as follows:

|  |  |  |
|---|---|---|
| (i) | BET surface | 60 m$^2$/g |
| (ii) | CTAB surface | 50 m$^2$/g |
| (iii) | oil uptake | 120 cm$^3$/100 g |
| (iv) | pH | 6.0 |

The chemical analyses of the resulting silica particles are reported in the following table:

| Ions | SO$_4$ | Al | Fe | Ca | C |
|---|---|---|---|---|---|
| ppm | 100 | 250 | 100 | 200 | 10 |

The surface chemistry was quantified by the following parameters:

Ho higher than 3.3
PZC=4.5
No pyridine adsorption bands

Compatibilities

| In-gredients | Fluoride (naF) | Pyrophosphate (Na/K) | Chlorhexidine (digluconate) | Zinc (ZnSO$_4$) |
|---|---|---|---|---|
| % Compatibility | 95 | 98 | 70 | 80 |

EXAMPLE 9

This example relates to the preparation of a silica thickening agent.

Into a reactor equipped with a turbine agitation system were introduced 5.07 l sodium silicate having a concentration in silica of 120 g/l, and a $SiO_2/Na_2O$ ratio of 3.5, and 3.8 l deionized water.

After commencing agitation (300 rpm), the contents of the reactor were heated to 68° C.

When this temperature was attained, 2.64 l sulfuric acid having a concentration of 80 g/l were added. The flow rate of the acid was 0.120 l/min.

After 22 min of addition, the addition of the acid was discontinued and the mixture was aged for 10 min (a sudden increase in turbidity was observed).

4.2 l sulfuric acid was then added over 35 min.

The temperature was increased to 87° C. and a simultaneous addition of sodium silicate, at a rate of 30 ml/min, and of sulfuric acid, at a rate of 52 ml/min, was carried out for 30 min.

The temperature was increased to 95° C. and 0.523 l sulfuric acid was added over 10 min.

The mixture was then aged for 10 min.

Finally, the pH of the medium was adjusted to 4 by the addition of acid.

The mixture was then filtered and the moist filter cake washed with deionized water until the conductivity of the filtrate was 100 microsiemens.cm$^{-1}$.

Another wash was carried out using water adjusted to pH 4, by addition of acetic acid thereto.

A final wash was performed with deionized water.

The product was then dried by atomization and micronized in a JET Pulverizer type grinder to produce a grain size of 1.2 microns.

The physico/chemical properties of the resulting silica particles were as follows:

|  |  |  |
|---|---|---|
| (i) | BET surface | 180 m$^2$/g |
| (ii) | CTAB surface | 170 m$^2$/g |
| (iii) | oil uptake | 350 cm$^3$/100 g |
| (iv) | pH | 6.8 |

The chemical analyses of the resulting silica particles are reported in the following table:

| Ions | SO$_4$ | Al | Fe | Ca | C |
|---|---|---|---|---|---|
| ppm | 500 | 200 | 120 | 300 | 10 |

The surface chemistry was quantified by the following parameters.

Ho higher than 3.3
PZC=3.6
No pyridine adsorption bands

Compatibilities

| In-gredients | Fluoride (naF) | Pyrophosphate (Na/K) | Chlorhexidine (digluconate) | Zinc (ZnSO$_4$) |
|---|---|---|---|---|
| % Compatibility | 90 | 95 | 70 | 60 |

EXAMPLE 10

In this example, the preparation of the silica filter cake used as the starting material for the silica produced in Examples 11 to 15 is described.

Into a 30 l reactor equipped with a temperature and pH control system and a Mixel type agitation system, 1.4 l sodium silicate having a $SiO_2/Na_2O$ ratio of 3.45 and a $SiO_2$ concentration of 135 g/l, preheated to 75° C., were introduced. After commencing agitation (300 rpm), the contents of the reactor were heated to 85° C.

When this temperature was attained, simultaneously, the same sodium silicate was added at a rate of 0.28 l/min, as well as sulfuric acid having a concentration of 80 g/l, preheated to 75° C., at a rate of 0.16 l/min.

The average pH of the medium during the simultaneous addition was 9.8.

After 47 min of simultaneous addition, the silicate addition was discontinued and the acid addition was continued at the same rate to provide a pH of 8. At this point, the reaction mixture was heated to 95° C. over 10 min, while continuing the addition of the acid to stabilize the pH of the reaction mixture at 4.2 at this temperature.

The mixture was then aged for 15 min at this pH and at 95° C.

The mixture was subsequently filtered and the moist filter cake was washed with deionized water until the conductivity of the filtrate was 2,000 µS/cm.

The cake obtained at this point was used as the base for the preparation of the controlled surface chemistry silica of Examples 11 to 15.

EXAMPLE 11

The filter cake produced in Example 10 was used.

The cake was dispersed in deionized water to form a suspension of 100 g/l silica and the suspension was then filtered. The operation was repeated until a conductivity of the filtrate of 100 microsiemens.cm$^{-1}$ was attained.

The cake was then redispersed in the form of a 150 g/l suspension in deionized water and the pH of the latter was adjusted to 6 by the addition of acetic acid.

After filtering, a final wash was carried out with deionized water.

The product was then dried by atomization and ground in a forplex type grinder to produce a grain size of 9.0 µm.

EXAMPLE 12

A cake obtained according to Example 10 was washed in deionized water until a conductivity of the filtrate of 500 microsiemens.cm$^{-1}$ was obtained.

The cake was then redispersed in the form of a 150 g/l suspension in deionized water and the pH of the latter was adjusted to 6 by the addition of acetic acid.

Under agitation, 25 g barium hydroxide Ba(OH)$_2$.8H$_2$O were added and the mixture aged for 30 min.

The suspension was then filtered and washed with 5 l water.

The product was dried by atomization and ground on a forplex type grinder to produce a grain size of 9.0 microns.

EXAMPLE 14

A filter cake produced according to the procedure of Example 10 was washed in deionized water until a conductivity of the filtrate of 100 microsiemens.cm$^{-1}$ was attained.

The cake was subsequently dispersed in the form of a 150 g/l suspension in deionized water and the pH of the latter was adjusted to 6.3 by the addition of acetic acid.

A final wash was carried out with deionized water.

Under agitation, 0.1 g barium acetate, (Ba(C$_2$H$_3$O$_2$)$_2$.H$_2$O) was added and the mixture aged for 30 min.

The product was then dried by atomization and ground on a forplex type grinder to produce a grain size of 9.0 microns.

EXAMPLE 15

The filter cake of Example 10 was used. The cake was dispersed in deionized water to form a 100 g/l silica suspension and the suspension was then filtered. The operation was repeated to produce a conductivity of the filtrate of 200 microsiemens.cm$^{-1}$.

The product was then dried by atomization and ground on a forplex type grinder to produce a grain size of 9.0 microns.

The properties of the silica particulates of Examples 11 to 15 are reported in the following table:

| Example | Surfaces (m$^2$/g) | | pH | OH/nm$^2$ | Oil uptake | PZC | Ho | Refractive index |
| --- | --- | --- | --- | --- | --- | --- | --- | --- |
| | BET | CTAB | | | | | | |
| 11 | 250 | 50 | 6.9 | 12 | 102 | 4.5 | >3.3 | 1.460 |
| 12 | 250 | 45 | 6.8 | 10 | 110 | 4 | >3.3 | 1.457 |
| 13 | 250 | 60 | 7.2 | 12 | 105 | 3.8 | >3.3 | 1.458 |
| 14 | 260 | 55 | 7.0 | 10 | 105 | 6 | >3.3 | 1.457 |
| 15 | 250 | 55 | 7.5 | 12 | 100 | 3.6 | >3.3 | 1.446 |

The cake was then washed with 10 l water adjusted to pH 4 by the addition of gluconic acid.

A final wash was effected with deionized water.

The cake was comminuted to produce a homogeneous suspension and 8.5 g barium acetate were added under agitation (Ba(C$_2$H$_3$O$_2$)$_2$. H$_2$O). The mixture was permitted to age for 30 min.

The product was then dried by atomization and ground in a forplex type grinder to produce a grain size of 9.0 µm.

EXAMPLE 13

The filter cake produced according to the procedure of Example 10 was washed with deionized water until a

| | Ions (ppm) | | | | |
| --- | --- | --- | --- | --- | --- |
| Examples | SO$_4$ | Al | Fe | Ca | C |
| 11 | 70 | 300 | 150 | 300 | 20 |
| 12 | 150 | 350 | 200 | 350 | 20 |
| 13 | 200 | 400 | 200 | 350 | 50 |
| 14 | 50 | 230 | 120 | 120 | 20 |
| 15 | 200 | 415 | 200 | 355 | 20 |

Compatibilities

| Examples | Fluoride (NaF) | Pyrophosphate (Na/K) | Chlorhexidine (digluconate) | Zinc (ZnSO$_4$) |
|---|---|---|---|---|
| 11 | 90 | 95 | 75 | 70 |
| 12 | 95 | 98 | 80 | 85 |
| 13 | 96 | 95 | 70 | 65 |
| 14 | 95 | 96 | 98 | 80 |
| 15 | 95 | 95 | 70 | 60 |

COMPARATIVE EXAMPLE 16

As a comparison, in the following table are reported the measurements of compatibility of the commercial silica generally used in dentifrice formulations, together with the physico/chemical properties thereof wherein $CH_x$=chlorhexidine, F=fluorine, Zn=zinc and PYR=pyrophosphate.

The measurements were performed by the tests described above.

| Silica (trademark of manufacturer) | Surfaces (m$^2$/g) CTAB | BET | Ho | OH/nm$^2$ | SO$_4$ (% by weight) | Compatibilities $CH_x$ | F | Zn | PYR |
|---|---|---|---|---|---|---|---|---|---|
| Hubert Zeodent 113 | 50 | 100 | <3 | 30 | 0.65 | 1 | 95 | 0 | 95 |
| Zeofinn Z113 | 70 | 175 | <3 | 17 | 0.50 | 1 | 96 | 0 | 95 |
| Grace Syloblanc 81 | 240 | 400 | <3 | 17 | 1.56 | 0 | 90 | 40 | 95 |
| Grace Syloid 244 |  | 400 | <3 | 17 | 0.7 | 4 | 90 | 2 | 90 |
| Degussa Sipernat 22S | 180 | 190 | <3 | 16 | 1.0 | 0 | 90 | 20 | 90 |
| Rhone Poulenc Tixosil 53 | 50 | 250 | <3 | 30 | 0.8 | 0 | 60 | 0 | 90 |

It should be noted that the pH was less than 3 for all materials reported in the table.

EXAMPLE 17

This example relates to the formulation of a translucid, gel type dentifrice composition incorporating the silica particulates of the invention.

The formula was as follows:

| | |
|---|---|
| (i) Sorbitol (70% aqueous) | 65.00 |
| (ii) Glycerin | 0.00 |
| (iii) CMC 7mFD | 0.80 |
| (iv) Sodium saccharinate | 0.20 |
| (v) Sodium fluoride | 0.24 |
| (vi) Sodium benzoate | 0.08 |
| (vii) Perfume | 2.00 |
| (viii) Abrasive silica, Example 5 | 15.00 |
| (ix) Thickening silica, Example 9 | 8.00 |
| (x) Chlorhexidine digluconate | 1.00 |
| (xi) Distilled water | 7.68 |

The dentifrice had satisfactory rheological properties and extruded suitably, both initially and after storage (2 months).

Visual examination of the dentifrice confirmed that the strength of the extrusion was proper and that it was present in the form of a translucid gel.

This dentifrice had the following properties:

| | |
|---|---|
| pH, dilution at 10%: | 6.8 |
| Abrasive strength on copper, LNE standard (mg): | 5.6 |
| Plastic viscosity (Pa · s): | 0.5 |

Anti-bacterial activity was present.

EXAMPLE 18

This example relates to the formulation of an opaque paste type dentifrice:

The formula was as follows:

| | |
|---|---|
| (i) Glycerin: | 22.00 |
| (ii) CMC 7MFD: | 1.0 |
| (iii) Sodium saccharinate: | 0.20 |
| (iv) Sodium monofluorophosphate: | 0.76 |
| (v) Sodium fluoride: | 0.10 |
| (vi) Sodium lauryl sulfate (30% aqueous): | 4.67 |

-continued

| | |
|---|---|
| (vii) Sodium benzoate: | 0.10 |
| (viii) Perfume: | 0.90 |
| (ix) Titanium dioxide: | 1.00 |
| (x) Abrasive silica, Example 8: | 31.50 |
| (xi) ZnSO$_4$.7H$_2$O: | 0.48 |
| (xii) Distilled water: | 37.29 |

Rheological and visual examination of the resulting dentifrice evidenced that the usual properties of the dentifrice were good.

Embodiment III

In a third embodiment of the present invention, the novel silica particulates are improvedly compatible with the aforementioned organic amino compounds and particularly the above described class of fluorine-containing amines and betaines. These silica particulates are characterized in that the pH of an aqueous suspension thereof varies as a function of its concentration and its electrical conductivity in accordance with the equations given above.

As indicated above, the essential characteristics of the silica particulates of the invention reside in the surface chemistry thereof. More specifically, one of the aspects to be taken into account in this surface chemistry is the acidity. The term "acidity" is used in the sense described in Embodiment II, above. More particularly, the acidity function Ho is used to characterize the silica particulates of the present embodiment. Ho is determined in the manner described above in Embodiment II. The protocol for measuring the pH as a function of the concentration of the aqueous silica suspension and its electrical conductivity has been described above in Embodiment I.

The surface state of the silica according to the invention is such that conditions regarding the number of acid surface sites are observed. This number may be measured as the number of $OH^-$ or silanol groups per $nm^2$, the procedure of which was described Embodiment I.

In the present case, the silica particulates of the present aspect of the invention advantageously have a number of $OH^-/nm^2$ equal to or less than 12, preferably at most 10, and more particularly ranging from 6 to 10.

The nature of the $OH^-$ sites of the silica particulates of the invention, which is also a characteristic of their surface chemistry, too may be evaluated by the zero charge point. The point of zero charge is defined by the pH of a silica suspension for which the electric charge of the surface of the solids is zero, regardless of the ionic strength of the medium. This (ZCP) measures the real pH of the surface, to the extent that it is free from all ionic impurities. The (ZCP) is determined as described in Embodiment I.

In practice, it is preferred that the (ZCP) be at least 4, advantageously ranging from 4 to 6. For a better compatibility with the metal cations, it is at most 6.5. For good compatibility with fluorine values, the (ZCP) is preferably at most 7.

Moreover, in order to improve the compatibility of the silica particulates according to this embodiment of the invention with respect to other constituents and in particular fluorine, the content of divalent and higher valency cations contained in the silica is at most equal to 1,000 ppm. It is particularly desirable that the aluminum content of the silica particulates of the invention be at most 500 ppm. Moreover, the iron content of the silica particulates of the invention is advantageously at most 200 ppm. Preferably, the calcium content is at most 500 ppm and more preferably at most 300 ppm.

The silicas according to the present embodiment preferably also have a carbon content of at most 50 ppm and particularly at most 10 ppm.

The silica particulates according to the present embodiment, which are compatible with organic amino compounds, are also compatible with the different metal cations contained in dentifrice compositions. Thus, the latter can comprise, inter alia, metal cations having a valency greater than 1 and which are provided by active molecules. For example, representative thereof are the divalent and higher valency metal cations of Groups IIa, IIIa, IVa and VIII of the Periodic Table. Particularly exemplary are the cations of Group IIa, namely, calcium, strontium and barium, cations of Group IIIa, namely, aluminum and indium, of Group IVa, namely, germanium, tin and lead and of Group VIII, namely, manganese, iron, nickel, zinc, titanium, zirconium, palladium, etc.

Such cations may be in the form of mineral salts thereof, e.g., chloride, fluoride, nitrate, phosphate or sulfate, or in the form of organic salts, e.g., acetate, citrate, etc. More specific examples include zinc citrate, zinc sulfate, strontium chloride, tin fluoride in the form of the single salt ($SnF_2$) or in the form of the double salt ($SnF_2/KF$), stannous chlorofluoride SnClF and zinc fluoride ($ZnF_2$).

The silica particulates, according to this embodiment of the invention, are compatible with the different metal cations. The compatibility of the subject silicas with such cations, as determined by the tests given below, is at least approximately 50%, preferably at least 70% and more preferably at least 80%.

These silica particulates can consequently be formulated with advantage into dentifrice compositions containing divalent and higher valency cations and more particularly in compositions incorporating at least one of the following components: zinc citrate, zinc sulfate, strontium chloride and tin fluoride.

In a preferred embodiment of the invention, the novel silica particulates are also compatible with guanidines and in particular chlorhexidine. The compatibility, measured by the tests given below, is at least approximately 30%. It can be improved to at least 60% and preferably to at least 90%.

In this case, the silica has a content of anions of the type $SO_4^{2-}$, $Cl^-$, $NO_3^-$, $PO_4^{3-}$, $CO_3^{2-}$ of at least $5.10^{-3}$ mole/100 g of silica. The lower this content, the higher will be the compatibility. In a preferred embodiment, it is at most $1.10^{-3}$ moles and more particularly $0.2.10^{-3}$ moles/100 g of silica.

In the case of silicas prepared from sulfuric acid, such anion content is more appropriately expressed by a content in $SO_4^=$ and by weight. In this event, the content is at the most 0.1%. In another preferred embodiment of the invention, such content is at most 0.05% and more particularly at most 0.01%.

Thus, the silica particulates according to the invention are particularly well suited for use in dentifrice compositions containing guanidines and bisguanides. Such compositions are described in U.S. Pat. Nos. 3,934,002 and 4,110,083, hereby incorporated by reference.

The pH of the silica particulates according to the invention, measured according to standard NFT 45-007, is generally at most 8 and preferably it ranges from 6.0 to 7.5.

The above characteristics provide a silica compatible with the aforementioned organic amino compounds, metal cations and, depending upon the particular case, also with fluorides and guanidines, in particular chlorhexidine.

In addition to the surface chemistry characteristics described above, which impart compatibility thereto, the silica particulates of this aspect of the invention also have physical properties which are perfectly suited for their use in a dentifrice. These physical/structural properties have been more fully described above.

Process for the Preparation of Novel Silica Particulates

The process for the preparation of the silica particulates of this aspect of the invention will now be described in greater detail. As indicated above, this process is of the type comprising reacting a silicate with an acid, resulting in the formation of a silica suspension or a silica gel.

It will be appreciated that any known operation may be used to prepare this suspension or gel (addition of acid to a silicate sediment, simultaneous total or partial addition of acid and silicate to a water sediment, or silicate solution, etc.), with the selection being made essentially as a function of the physical characteristics of the silica which is sought to be produced.

In this embodiment, preferably, the silica gel or suspension is prepared by simultaneously adding the silicate and the acid to a sediment, which can be a water sediment, a colloidal silica dispersion containing 0 to 150 g/l of silica, expressed as $SiO_2$, a silicate or an inorganic or organic salt, preferably of alkali metals, such as, e.g., sodium sulfate or sodium acetate. The addition of these two reagents is carried out simultaneously in such manner that the pH is maintained constant at a value of from 4 to 10, preferably from 8.5 to 9.5. The temperature advantageously ranges from 60° to 95° C.

One technique for preparing the colloidal silica dispersion, preferably having a concentration of from 20 to 150 g/l entails heating an aqueous silicate solution, e.g., at a temperature of from 60° to 95° C., and adding the acid to said aqueous solution until a pH is obtained ranging from 8.0 to 10.0 and preferably close to 9.5.

The concentration of the aqueous silicate solution, expressed as $SiO_2$, preferably ranges from 20 to 150 g/l. It is possible to use a diluted or concentrated acid, and its normality can range from 0.5 to 36N, preferably from 1 to 2N.

The silicate is advantageously an alkali metal silicate and preferably a sodium silicate, with a $SiO_2/Na_2O$ weight ratio of from 2 to 4 and preferably equal to 3.5. The acid can be gaseous, such as carbon dioxide gas, or liquid, preferably sulfuric acid.

In a further stage of the process of this embodiment, the suspension or gel is subjected to a plural aging operation. A first aging is carded out at a pH of at most 8.5 and, e.g., ranging from 6 to 8.5 and preferably at 8.0. Aging is preferably carried out hot, e.g., at a temperature of from 60° to 100° C. and preferably at 95° C. for a period of time ranging from 10 minutes to 2 hours.

A variant of this embodiment comprises preparing a silica gel or a silica suspension by progressively adding the acid to a sediment containing the silicate, until the desired aging pH is attained. This operation is carried out at a temperature preferably ranging from 60° to 95° C. The suspension of the silica gel is then aged under the conditions described hereinbefore.

This is followed by a second aging at a pH below 6, preferably ranging from 5 to 6 and even more preferably is equal to 5.5. The temperature and time conditions are the same as for the first aging step. Acid is added to attain the desired aging pH.

It is also possible to use an inorganic acid such as nitric, hydrochloric, sulfuric or phosphoric acid, or even carbonic acid formed by bubbling carbon dioxide gas.

A third aging step is then carried out, at a pH below 5, preferably from 3 to 5, and even more preferably about 4.

The temperature and time conditions are the same as for the two other aging operations. Acid is added to obtain the desired aging pH. The silica is then separated from the reaction medium by any known means, such as, e.g., a vacuum filter or a filter press. Thus, a silica cake is recovered.

The process according to this embodiment can then proceed according to two principal variants.

The first variant relates to the preparation of silicas compatible with the organic amino compounds and the divalent and higher valency metal cations. In this case, the process entails washing the cake under conditions such that the pH of the suspension or the medium before drying must comply with the following equation:

$$pH = d - e \log(D) \quad \text{(III)}$$

in which $e$ is a constant equal to or greater than 0.6 and equal to or less than 1.0; $d$ is a constant equal to or greater than 7.0 and equal to or less than 8.5; and (D) represents the electrical conductivity of the aqueous silica suspension, expressed in microsiemens.cm$^{-1}$.

The washing is advantageously with water, preferably deionized water, and/or using an acid solution having a pH of from 2 to 7.

This acid solution may be, for example, a solution of an inorganic acid such as nitric acid.

However, preferably, said acid solution can also be a solution of an organic acid, particularly a complexing organic acid. This acid can be selected from among carboxylic, dicarboxylic, hydroxycarboxylic and aminocarboxylic acids. Examples of such acids are acetic acid and examples of the complexing acids are tartaric, maleic, glyceric, gluconic and citric acids.

Particularly when using a solution of an inorganic acid, it can be advantageous to carry out a final washing with deionized water.

The second variant relates to the preparation of silicas which are also compatible with guanidines and, in particular, chlorhexidine.

In this case, a more pronounced washing is carried out. It must be continued until a washing filtrate is obtained, whose conductivity is at the most 200 microsiemens-cm$^{-1}$ and preferably below 100 microsiemens.cm$^{-1}$. As indicated above, it is important that the anion concentration is at most $5.10^{-3}$ mole/100 g of silica.

As a function of the particular case, it is possible to carry out one or more washing operations, typically two such washing with water and preferably deionized water and/or with an aqueous solution of an organic acid, particularly those indicated above.

From a practical standpoint, the washing operations can be carried out by pouring the washing solution onto the cake, or by introducing the latter into the suspension obtained, following the crumbling of the cake. Thus, the filter cake, prior to the drying operation, is subjected to crumbling or disintegration, which can be carried out by any known means, e.g., a high speed stirrer.

Thus, before or after washing, the silica cake is comminuted and then dried by any known means. Drying can be carried out in a tunnel or muffle furnace, for example, or by atomization in a hot air stream, the inlet temperature of which can range from approximately 200° to 500° C. and whose outlet temperature ranges from approximately 80° to 100° C. The residence time advantageously ranges from 10 seconds to 5 minutes.

If necessary, the dried material can be ground to provide the desired grain or particle size. This operation is carried out in a conventional apparatus, such as an impeller mill or an air jet grinder.

Improved Dentifrice Compositions

The present embodiment of the invention also features novel dentifrice compositions containing the silicas described above, or prepared by the process also described above.

The amount of such silica incorporated in the dentifrice compositions of the present invention can vary over wide limits, but typically ranges from 5% to 35% by weight.

The silicas according to the present embodiment can be used more particularly in dentifrice compositions containing at least one constituent selected from among the fluorides, phosphates, guanidines and in particular chlorhexidine. Thus, they can have a compatibility, according to the tests given below, of at least 90% for each of these constituents.

They are also suitable for dentifrice compositions containing at least one constituent selected from among the organic amino compounds and compounds supplying a divalent and higher valency metal cation. They can then have a compatibility, also according to the tests given below, of up to 80% for each constituent.

The silicas according to this aspect of the invention are particularly well suited for dentifrice formulations simultaneously containing at least one inorganic fluoride and/or organic fluoride, at least one alkyl betaine and at least one guanidine, in particular chlorhexidine.

Preferred such formulations include a sodium fluoride and/or a tin fluoride and/or a fluorine-containing amine, more specifically cetyl amine hydrofluoride, bis-(hydroxyethyl)-aminopropyl-N-hydroxyethyl-octadecyl amine dihydrofluoride, an alkyl betaine and chlorhexidine.

The silicas according to the present embodiment are also compatible with maleic acid/vinyl ethyl ether copolymers and, therefore, can also be incorporated into dentifrice compositions comprising these copolymers.

The composition of a dentifrice including the novel silica particulates is more fully described above in Embodiment I.

Illustrative Examples

In order to further illustrate the present invention and the advantages thereof, the following specific examples are given, it being understood that same are intended only as illustrative and in nowise limitative.

In said examples to follow, the pH measuring protocol as a function of the conductivity and concentration, as well as the tests for measuring the compatibility of the silica with the various constituents, were carried out according to the following techniques:

pH Measurement protocol as a function of the silica concentration and its conductivity:

Silica suspensions having increasing concentrations ranging from 0% to 25% by weight were formed by dispersing a mass 100 $\underline{m}$ of degassed, deionized water (Millipore quality). The suspensions were stirred for 24 hours at 25° C.

The pH of the suspensions and solutions obtained after centrifuging a fraction of the suspension at 8,000 r.p.m. for 40 min, and filtering on a 0.22 μm Millipore filter, were measured at 25° C. under a nitrogen atmosphere using a Titroprocessor Metrohm 672-type measuring system.

In the same manner, the conductivity of the resulting suspensions and solutions was measured at 25° C. using a Radiometer conductivity meter (CDM83) equipped with a CDC304 cell with a cell constant equal to 1 cm$^{-1}$. The conductivity is reported in microsiemens/cm (μS/cm).

The suspension effect (SE) is defined as the difference in pH between the pH of a 20% silica suspension and the pH of its supernatant solution separated by centrifugation.

Measurement Of compatibility with bis-(hydroxyethyl)-aminopropyl-N-hydroxyethyl-octadecyl amine dihydrofluoride;

(1) An aqueous solution containing 1.65% of fluorine-containing amine was formed by adding 5 g of 33% fluorine-containing amine to propanediol in 95 g of twice distilled water.

(2) 4 g of silica were dispersed in 16 g of the solution produced in (1). The thus obtained suspension was stirred for 4 weeks at 37° C.

(3) The suspension was then centrifuged at 8,000 r.p.m. for 30 min and the supernatant obtained was filtered on a 0.22 μm Millipore filter.

(4) The free fluorine-containing amine concentration was determined by nitrogen microanalysis of the solution obtained in (1) and of the supernatant obtained in (3).

(5) The compatibility was determined by the following relationship:

$$\% \text{ compatibility} = \frac{N \text{ concentration in supernatant (3)}}{N \text{ concentration in solution (1)}} \times 100$$

Hereinafter, the percentage fluorine-containing amine compatibility is designated AF.

Measurement of compatibility with cetyl amine hydrofluoride:

(1) An aqueous solution containing 1.72% of fluorine-containing amine was formed by dissolving 1.72 g of cetyl amine hydrofluoride in 98.28 g of twice distilled water.

(2) 4 g of silica were dispersed in 16 g of the solution produced in (1). The thus obtained suspension was stirred for 4 weeks at 37° C.

(3) The suspension was then centrifuged at 8,000 r.p.m. for 30 min and the supernatant obtained was filtered on an 0.22 μm Millipore filter.

(4) The free fluorine-containing amine concentration was determined by nitrogen microanalysis of the solution obtained in (1) and of the supernatant obtained in (3).

(5) The compatibility was determined by the following relationship:

$$\% \text{ compatibility} = \frac{N \text{ concentration in supernatant (3)}}{N \text{ concentration in solution (1)}} \times 100$$

Hereinafter, the percentage fluorine-containing amine compatibility is designated AFc.

Measurement of compatibility with an alkyl betaine:

The alkyl betaine used was the product marketed by AKZO under the trademark ARMOTERIC LB.

(1) An aqueous solution containing 2% alkyl betaine was formed by dissolving 6.67 g of 30% alkyl betaine in 93.33 g of twice distilled water.

(2) 4 g of silica were dispersed in 16 g of the solution produced in (1). The thus obtained suspension was stirred for 4 weeks at 37° C.

(3) The suspension was then centrifuged at 8,000 r.p.m. for 30 min and the supernatant obtained was filtered on an 0.22 μm Millipore filter.

(4) The free alkyl betaine concentration was determined by organic carbon microanalysis of the solution obtained in (1) and the supernatant obtained in (3).

(5) The compatibility was determined by the following relationship:

$$\% \text{ compatibility} = \frac{N \text{ concentration in supernatant (3)}}{N \text{ concentration in solution (1)}} \times 100$$

Hereinafter, the percentage alkyl betaine compatibility is designed aBeta.

Measurement Of compatibility with an alkylamidoalkyl betaine:

(1) An aqueous solution containing 2.0% alkylamidoalkyl betaine was formed by dissolving 6.67 g of 30% alkylamidoalkyl betaine in 93.33 g of twice distilled water.

(2) 4 g of silica were dispersed in 16 g of the solution produced in (1). The thus obtained suspension was stirred for 4 weeks at 37° C.

(3) The suspension was then centrifuged at 8,000 r.p.m. for 30 min and the supernatant obtained was filtered on an 0.22 μm Millipore filter.

(4) The free alkylamidoalkyl betaine concentration was determined by organic carbon microanalysis of the solution obtained in (1) and the supernatant obtained in (3).

(5) The compatibility was determined by the following relationship:

$$\% \text{ compatibility} = \frac{N \text{ concentration in supernatant (3)}}{N \text{ concentration in solution (1)}} \times 100$$

Hereinafter, the percentage alkylamidoalkyl betaine compatibility is designated by Beta.

Measurement of compatibility width chlorhexidine:

4 g of silica were dispersed in 16 g of an aqueous chlorhexidine solution having a 1% concentration in chlorhexidine digluconate. The suspension was stirred for 24 hours at 37° C. The suspension was then centrifuged at 20,000 r.p.m. for 30 min and the supernatant obtained was filtered on an 0.2 μm Millipore filter. 0.5 ml of the thus filtered solution was sampled and diluted in 100 ml of water in a graduated flask. This solution formed the test solution.

A reference solution was formed using the same protocol, but without the silica. A 1% chlorhexidine digluconate aqueous solution was stirred for 24 hours at 37° C., centrifuged at 20,000 r.p.m. and the supernatant filtered on an 0.2 μm Millipore filter. 0.5 ml of the thus obtained solution was diluted in 100 ml of water in a graduated flask.

The absorptivity of the two solutions was then measured at 254 nm using a spectrophotometer (Uvikon 810/820).

The free chlorhexidine quantity ($CH_x$), designated % compatibility, was determined by the relationship:

$$\% \text{ compatibility} = \frac{\text{Test absorptivity}}{\text{Reference absorptivity}} \times 100$$

Measurement of compatibility with zinc, fluorides, and sodium and potassium pyrophosphates was as described above.

EXAMPLE 19

Into a reactor equipped with a temperature and pH regulating system and a propeller stirring system (Mixel), were introduced 8.32 liters of sodium silicate having a 130 g/l silica concentration and a $SiO_2/Na_2O$ molar ratio of 3.5 and 8.33 liters of soft water having a conductivity of 1 μS/cm. After beginning stirring (350 r.p.m.), the thus formed sediment was heated at 90°20 C. When the desired temperature was attained, sulfuric acid having a concentration of 80 g/l was added at a constant flow rate of 0.40 l/min in order to adjust the pH to 9.5.

This was followed by the simultaneous addition of 45.25 l of sodium silicate having a silica concentration of 130 g/l, a $SiO_2/Na_2O$ molar ratio of 3.5 and a flow rate of 0.754 l/min and 29.64 l of 80 g/l sulfuric acid. The sulfuric acid rate was adjusted such as to maintain the pH of the reaction medium at a constant value of 9.5.

After adding for 60 min, the sodium silicate addition was terminated and sulfuric acid addition continued at a rate of 0.494 l/min until the pH of the reaction mixture was stabilized at 8. During this phase, the temperature of the medium was increased to 95° C. This was followed by aging for 30 min at said pH and at 95° C. During aging, the pH was maintained at 8 by adding acid.

Upon completion of aging, the pH was adjusted to 5.5 by adding sulfuric acid at a flow rate of 0.494 l/min and this was followed by aging for 30 min at said pH and at 95° C. Upon completion of aging, the pH was adjusted to 3.5 by adding sulfuric acid and was maintained at this level for 30 min.

After discontinuing the heating, the mixture was filtered and the cake obtained washed with deionized water until a filtrate having a conductivity of 2000 μS/cm was obtained. The cake obtained after washing was dispersed in the presence of deionized water to form a suspension having a silica concentration of 10%. The pH of the suspension was adjusted to 6 by adding acetic acid.

Thereafter, a second filtration was carried out, and then a water washing, such as to adjust the conductivity to 500 μS/cm and water washing with a pH adjusted to 5 by acetic acid, such as to adjust the pH to 5.5. The medium was then monitored to ensure that the following relationship existed:

$pH \leq 8.20 - 0.91 \log(D)$.

The cake was then crumbled and the silica dried by atomization. Thereafter, the silica obtained was ground on an impeller mill in order to produce a powder, the average agglomerate diameter of which, measured on a COULTER counter, was 8 μm.

The physico/chemical characteristics of the thus obtained silica are indicated in the following table:

| | |
|---|---|
| BET surface, m²/g | 65 |
| CTAB surface, m²/g | 60 |
| DOP oil absorption, ml/100 g of silica | 125 |
| Pore volume, Hg, cm³/g | 1.90 |
| pH (5% water) | 6.2 |
| Refractive index | 1.450 |
| Translucency % | 90 |
| $Na^+$ ppm | 60 |
| $SO_4^=$ ppm | 100 |
| $Al^{3+}$ ppm | 200 |
| $Fe^{3+}$ ppm | 120 |
| $Ca^{2+}$ ppm | 30 |
| $Cl^-$ ppm | 20 |
| C ppm | 5 |

Table II below reports the surface chemistry characteristics of the silica according to the invention, as well as the results of the compatibility with the organic amino compounds. Table III reports the compatibility results with the conventional components of dentifrice formulations, namely, chlorhexidine, fluoride, zinc and pyrophosphate.

EXAMPLE 20

Into a reactor equipped with a temperature and pH regulating system and a propeller stirring system (Mixel) were introduced 530 l of sodium silicate having a silica concentration of 135 g/l and a $SiO_2/Na_2O$ molar ratio of 3.5 and 15 l of soft water having a conductivity of 1 μS/cm. After actuating the stirring system (350 r.p.m.), the thus formed sediment was heated to 90° C. When this temperature was attained, sulfuric acid having a concentration of 80 g/l was added at a constant flow rate of 0.38 l/min to adjust the pH to 9.5.

This was followed by the simultaneous addition of 44.70 l of sodium silicate having a 135 g/l silica concentration, a $SiO_2/Na_2O$ molar ratio of 3.5 and a flow rate of 0.745 l/min and 25.30 l of 80 g/l sulfuric acid. The sulfuric acid rate was adjusted such as to maintain the pH of the reaction medium at a constant value of 9.5.

After 60 min of addition, the sodium silicate addition was terminated and sulfuric acid addition was continued at a rate of 0.350 l/min until the pH of the reaction mixture was stabilized at 8. During this phase, the temperature of the medium was increased to 95° C. This was followed by aging for 30 min at this pH and at 95° C. During aging the pH was maintained at 8 by acid addition. Upon completion of aging the pH was adjusted to 5 by adding sulfuric acid at a rate of 0.400 l/min and subsequently another aging was carried out for 30 min at said pH and at 95° C. Upon completion of this aging, the pH was adjusted to 3.5 by adding sulfuric acid and said pH was maintained at 3.5 for 30 min.

After discontinuing heating, the mixture was filtered and the cake obtained washed with deionized water until a filtrate was obtained having a conductivity of 2000 μS/cm. The cake was then crumbled in the presence of water to form a 20% silica suspension and the pH was adjusted to 5.1 such as to ensure that the following relationship existed:

$pH \leq 8.20 - 0.91 \log(D)$.

The silica was dried by atomization and ground on an impeller mill to produce a powder, the mean agglomerate diameter of which was 8 μm.

The physico/chemical characteristics of the thus obtained silica are indicated below:

| | |
|---|---|
| BET surface, m²/g | 100 |
| CTAB surface, m²/g | 80 |
| DOP oil absorption, ml/100 g of silica | 200 |
| Pore volume, Hg, cm³/g | 3.35 |
| pH (5% water) | 6.5 |
| Refractive index | 1.455 |
| Translucency % | 95 |
| $SO_4^=$ % | 0.5 |
| $Na^+$ % | 0.25 |
| $Al^{3+}$ ppm | 350 |
| $Fe^{3+}$ ppm | 120 |
| $Ca^{2+}$ ppm | 50 |
| $Cl^-$ ppm | 20 |
| C ppm | 5 |

Table II below reports the surface chemistry characteristics of the silica according to the invention, as well as the compatibility results with the organic amino compounds. Table III reports the compatibility results with the conventional components of dentifrice formulations, namely chlorhexidine, fluoride, zinc and pyrophosphate.

EXAMPLE 21

Into a reactor equipped with a temperature and pH regulating system and a propeller stirring system (Mixel) were introduced 5.60 l of sodium silicate having a silica concentration of 135 g/l and a $SiO_2/Na_2O$ molar ratio of 3.5.

After actuating the stirring system (350 r.p.m.), the thus formed sediment was heated to 85° C. When this temperature was attained, sulfuric acid having a concentration of 85 g/l and preheated to 70° C. was added at a constant flow rate of 0.50 l/min in order to adjust the pH to 9.7.

This was followed by the simultaneous addition of 52.64 l of sodium silicate having a 135 g/l silica concentration, a molar ratio $SiO_2/Na_2O$ of 3.5 and at a rate of 0.745 l/min and 30 l of 85 g/l sulfuric acid. The sulfuric acid rate was adjusted such as to maintain the pH of the reaction medium at a constant value of 9.7. The simultaneous addition was carried out at 85° C. using reagents preheated to 70° C.

After continuing the additions for 45 min, sodium silicate addition was terminated and sulfuric acid addition continued at a rate of 0.450 l/min until the pH of the reaction mixture was stabilized at 8. During this phase, the temperature of the medium was increased to 95° C. This was followed by aging for 10 min at said pH and 95° C. During aging, the pH was maintained at 8 by adding acid. Upon completion of aging the pH was adjusted to 5 by adding sulfuric acid at a rate of 0.750 l/min and this was followed by a second aging for 15 min at said pH and 95° C. Upon completion of this aging, the pH was adjusted to 3.7 by adding sulfuric acid and said pH level was maintained for 60 min.

After discontinuing heating the mixture was filtered and the cake obtained washed with deionized water until a filtrate having a conductivity of 2500 μS/cm was obtained. The cake was then crumbled in the presence of water to form a 20% silica suspension and the pH was adjusted to 5.5 to ensure that the following relationship existed:

$pH \leq 7.5 - 0.70 \log (D)$.

The silica was dried by atomization and ground on an impeller mill to produce a powder having a mean agglomerate diameter of 8 μm.

The physico/chemical characteristics of the thus obtained silica are indicated in the following table:

| | |
|---|---|
| BET surface, m²/g | 200 |
| CTAB surface, m²/g | 55 |
| DOP oil absorption, ml/100 g of silica | 110 |
| Pore volume, Hg, cm³/g | 2.65 |
| pH (5% water) | 7.0 |
| Refractive index | 1.460 |
| Translucency % | 85 |
| $SO_4^=$ % | 200 |
| $Na^+$ % | 60 |
| $Al^{3+}$ ppm | 150 |
| $Fe^{3+}$ ppm | 120 |
| $Ca^{2+}$ ppm | 50 |
| $Cl^-$ ppm | 20 |
| C ppm | 5 |

The following Table II reports the surface chemistry characteristics of the silicas of the invention described in Examples 19 to 21. It also reports the compatibility results of the silicas according to the invention with organic amino compounds.

Table III reports the compatibility results with the conventional components used in dentifrice formulations, namely, chlorhexidine, fluoride, zinc and pyrophosphate.

For comparison purposes, Tables II and III provide the characteristics and different compatibilities of commercially available silicas, the following list constituting a representative range thereof:

S81: Syloblanc 81 (GRACE)

Z113: Zeodent 113 (HUBER)

Sid12: Sident 12 (DEGUSSA)

Syl15: Sylox 15 (GRACE)

T73: Tixosil 73 (RHONE-POULENC)

T83: Tixosil 83 (RHONE-POULENC).

TABLE II

Physicochemical characteristics and compatibility with organic amino compounds of silicas according to the invention and conventional silicas

| | Physicochemical characteristics of silicas | | | | | % compatibility | | |
|---|---|---|---|---|---|---|---|---|
| Silica | pH/log (C) | pH/log (D) | SE | Ho | ZPC | AF | Beta | CHx |
| S81 | 4.7–0.75x | 7.0–0.62z | −0.17 | ≦2 | 2.2 | 0 | 0 | 0 |
| Z113 | 8.1–0.94x | 10–1.0z | −0.70 | ≦3 | 2.5 | 0 | 0 | 0 |
| Sid12 | 7.6–0.55x | 8.5–0.60z | −0.20 | ≦3 | 2.8 | 0 | 0 | 0 |
| Syl15 | 8.1–0.70x | 9.2–0.74z | −0.94 | ≦3 | 2.5 | 0 | 0 | 0 |
| T73 | 8.6–0.81x | 10–0.87z | −0.20 | ≦3 | 3.0 | 0 | 0 | 0 |
| T83 | 7.5–0.60x | 8.6–0.60z | −0.18 | ≦3 | 2.5 | 0 | 0 | 0 |
| Example 19 | 7.5–0.30x | 8.0–0.50z | −0.00 | ≧4 | 4.2 | 85 | 60 | 95 |

TABLE II-continued

Physicochemical characteristics and compatibility with organic amino compounds of silicas according to the invention and conventional silicas

| Silica | Physicochemical characteristics of silicas | | | | | % compatibility | | |
|---|---|---|---|---|---|---|---|---|
| | pH/log (C) | pH/log (D) | SE | Ho | ZPC | AF | Beta | CHx |
| Example 20 | 6.5–0.80x | 8.2–0.90z | −0.10 | ≥4 | 4.5 | 85 | 50 | 30 |
| Example 21 | 7.0–0.40x | 7.4–0.60z | −0.06 | ≥4 | 4.0 | 80 | 50 | 90 |

The symbols used in the above Table have the following definitions: pH/log(C) represents the equation pH=b−a·log(C), in which $\underline{a}$ and $\underline{b}$ are two constants and C is the weight percentage of silica in the suspension; pH/log(D) represents the equation pH=b'−a'log(D), in which $\underline{b}'$ and $\underline{a}'$ are two constants and D is the conductivity of the silica suspension in μS/cm; SE represents the suspension effect measured by the relation SE=pH suspension−pH supernatant defined elsewhere; Ho is the Hammett constant; ZCP represents the pH for which the surface charge of the silica is zero; AF, Beta, and CHx represent the compatibility percentages of fluorine-containing amines, alkyl betaine and chlorhexidine respectively, such amounts being indicated above. The compatibility percentages obtained with fluorine-containing amine AFc and the alkyl betaine aBeta were similar to those obtained, respectively for AF and Beta.

TABLE III

Compatibility of silicas with the active molecules:

| Silica | % Compatibility | | | | | |
|---|---|---|---|---|---|---|
| | $P_2O_7^=$ | $Zn^{++}$ | $F^-$ | AF | Beta | CHx |
| S81 | 80 | 0 | 90 | 0 | 0 | 0 |
| Z113 | 90 | 0 | 95 | 0 | 0 | 0 |
| Sid12 | 80 | 10 | 90 | 0 | 0 | 0 |
| Sy115 | 80 | 0 | 90 | 0 | 0 | 0 |
| T73 | 90 | 20 | 90 | 0 | 0 | 0 |
| T83 | 95 | 10 | 95 | 0 | 0 | 0 |
| Example 19 | 95 | 80 | 95 | 85 | 60 | 95 |
| Example 20 | 90 | 75 | 95 | 85 | 50 | 30 |
| Example 21 | 95 | 80 | 95 | 80 | 50 | 90 |

The results of this Table evidence that the silicas according to the invention, more particularly compatible with organic amino compounds, differ markedly compared with the standard silicas in consideration of the following relationships:

$$pH \leq 8.5 - 0.40 \log (D) \text{ and } pH \geq 7.0 - 0.60 \log (D)$$

$$pH \leq 7.5 - 0.70 \log (C) \text{ and } pH \geq 5.0 - 0.50 \log (C)$$

Embodiment IV

A fourth embodiment of the present invention features novel silica particulates especially well adapted for compatibility with metal cations, in particular zinc, tin, strontium, and the like, as well as the fluorides.

According to this embodiment, the silica particulates advantageously have a number of $OH^-/nm^2$ (NOH) equal to or less than 10 and more particularly ranging from 4 to 10.

For the silicas according to this embodiment, ZCP ranges from 3 to 6.5.

The methods for determining NOH and ZCP are described above in Embodiment I.

Moreover, in order to improve the compatibility of the silica particulates according to this embodiment with respect to other constituents and in particular fluorine, the content of divalent and higher valency cations contained in the silica is at most equal to 1,000 ppm. It is particularly desirable that the aluminum content of the silica particulates of the invention be at most 500 ppm. Moreover, the iron content of the silica particulates of the invention is advantageously at most 200 ppm. Preferably, the calcium content is at most 500 ppm and more preferably at most 300 ppm.

The silicas according to this embodiment preferably also have a carbon content of at most 50 ppm and more preferably at most 10 ppm.

Finally, the pH of the silica particulates according to this embodiment, measured according to standard NFT 45-007, is generally at most 7 and preferably it ranges from 6 to 7.

The above characteristics provide a silica compatible with divalent and higher valency metal cations and in particular zinc, strontium and tin. This compatibility, measured by the test described below, is at least 30%, preferably at least 50% and more preferably at least 80%. In addition, the silicas according to this embodiment have a good compatibility with the fluoride anion, of at least approximately 80% and preferably at least 90%.

In addition to the surface chemistry characteristics described above, which impart compatibility thereto, the silica particulates of the invention also have physical properties which are perfectly suited for their use in a dentifrice.

Advantageously, the BET surface of the silica particulates of the invention ranges from 40 to 600 m²/g, and more preferably from 40 to 350 m²/g. Their CTAB surface typically ranges from 4 to 400 m²/g, and more preferably from 40 to 200 m²/g.

The BET surface is determined by the BRUNAUER-EMMET-TELLER method described in the *Journal of the American Chemical Society*, Vol. 60, p. 309 (February 1938) and according to the standard NF X11-622 (3.3).

The CTAB surface is the external surface determined by the ASTM standard D3785, but by using the adsorption of hexadecyltrimethyl ammonium bromide (CTAB) at pH 9 and taking 35 $A^{02}$ as the projected area of the CTAB molecule.

The silica of the invention may correspond to the three types usually distinguished in the dentifrice field.

Thus, the silica particles of the invention may be of the abrasive type. Same then have a BET surface of from 40 to 300 m²/g. In this case, the CTAB surface ranges from 40 to 100 m²/g.

The silica particles of the invention may also be of the thickening type. Their BET surface then ranges from 120 to 450 m²/g, and more preferably from 120 to 200 m²/g. They may have a CTAB surface of from 120 to 400 m²/g, and more preferably from 120 to 200 m²/g.

Finally, as a third type, the silica particles of the invention may be bifunctional. In this instance they have a BET surface of from 80 to 200 m²/g. Their CTAB surface ranges from 80 to 200 m²/g.

The silica particles of the invention may also exhibit an oil uptake of from 80 to 500 cm³/100 g determined by the NFT standard 30-022 (March 53) using dibutyl phthalate.

More precisely, such oil uptake ranges from 100 to 140 cm³/100 g for the abrasive silica, from 200 to 400 for the thickening silica and from 100 to 300 for the bifunctionals.

The silica particulates preferably have, again vis-a-vis their dentifrice applications, a particle size of from 1 to 10 μm.

This mean particle size is measured by Counter-Coulter.

The apparent density thereof generally ranges from 0.01 to 0.3. In a preferred embodiment of the invention, the silica particulates are precipitated silica particulates.

Finally, the silica of the invention has a refraction index generally from 1.440 to 1.465.

Process for the Preparation of Novel Silica Particulates

The process for the preparation of the silica particulates of this embodiment of the invention will now be described in greater detail. As indicated above, this process is of the type comprising reacting a silicate with an acid, resulting in the formation of a silica suspension or a silica gel.

It will be appreciated that any known operation may be used to prepare this suspension or gel (addition of acid to a silicate sediment, simultaneous total or partial addition of acid and silicate to a water sediment, or silicate solution, etc.), with the selection being made essentially as a function of the physical characteristics of the silica which is sought to be produced.

In a preferred embodiment, the silica gel or suspension is prepared by simultaneously adding the silicate and the acid to a sediment, which can be a water sediment, a colloidal silica dispersion containing 0 to 150 g/l of silica, expressed as $SiO_2$, a silicate or an inorganic or organic salt, preferably of alkali metals, such as, e.g., sodium sulfate or sodium acetate. The addition of these two reagents is carried out simultaneously in such manner that the pH is maintained constant at a value of from 4 to 10, preferably from 8.5 to 9.5. The temperature advantageously ranges from 60° to 95° C.

One technique for preparing the colloidal silica dispersion, preferably having a concentration of from 20 to 150 g/l entails heating an aqueous silicate solution, e.g., at a temperature of from 60° to 95° C., and adding the acid to said aqueous solution until a pH is obtained ranging from 8.0 to 10.0 and preferably close to 9.5.

The concentration of the aqueous silicate solution, expressed as $SiO_2$, preferably ranges from 20 to 150 g/l. It is possible to use a diluted or concentrated acid, and its normality can range from 0.5 to 36N, preferably from 1 to 2N.

The silicate is advantageously an alkali metal silicate and preferably a sodium silicate, with a $SiO_2/Na_2O$ weight ratio of from 2 to 4 and preferably equal to 3.5. The acid can be gaseous, such as carbon dioxide gas, or liquid, preferably sulfuric acid.

In a further stage of the process of this embodiment, the suspension or gel is subjected to a double aging operation. A first aging is carried out at a pH of at most 8.5 and, e.g., ranging from 6 to 8.5 and preferably at 8.0. Aging is preferably carded out hot, e.g., at a temperature of from 60° to 100° C. and preferably at 95° C. for a period of time ranging from 10 minutes to 2 hours.

Another variant of the present embodiment comprises preparing a silica gel or a silica suspension by progressively adding the acid to a sediment containing the silicate, until the desired aging pH is attained. This operation is carried out at a temperature preferably ranging from 60° to 95° C. The suspension of the silica gel is then aged under the conditions described hereinbefore.

This is followed by a second aging at a pH below 5, preferably ranging from 3 to 5 and even more preferably ranging from 3.5 to 4.0. The temperature and time conditions are the same as for the first aging step. Acid is added to attain the desired aging pH.

It is also possible to use an inorganic acid such as nitric, hydrochloric, sulfuric or phosphoric acid, or even carbonic acid formed by bubbling carbon dioxide gas.

The silica is then separated from the reaction medium by any known means, e.g., a vacuum filter or a filter press. Thus, a silica cake is recovered.

The next stage of the process according to this embodiment entails washing the silica cake thus produced. Washing is carried out under conditions such that the pH of the suspension or medium prior to drying is in accordance with the following equation:

$$pH = d - e \log (D) \qquad (II)$$

in which $e$ is a constant equal to or less than 1.0; $d$ is a constant equal to or less than 8.5; and (D) is the electrical conductivity of the aqueous silica suspension expressed in microsiemens.cm⁻¹ (μS/cm).

The washing is with water, preferably at a temperature ranging from 40 to 80° C. As a function of the particular case, one or more and generally two washing operations are carried out with water, preferably deionized water and/or using an acid solution having a pH of from 2 to 7. This acid solution may be, for example, a solution of an inorganic acid such as nitric acid.

However, preferably, said acid solution can also be an organic acid solution, particularly of a complexing organic acid. This acid can be selected from among carboxylic, dicarboxylic, hydroxycarboxylic and aminocarboxylic acids.

One example of such an acid is acetic acid and examples of the complexing acids are tartaric, maleic, glyceric, gluconic and citric acid.

Particularly when using a solution of an inorganic acid, it can be advantageous to carry out a final washing with deionized water.

From a practical standpoint, the washing operations can be carried out by pouring the washing solution onto the cake, or by introducing the latter into the suspension obtained, following the crumbling of the cake. Thus, the filter cake, prior to the drying operation, is subjected to crumbling or disintegration, which can be carried out by any known means, e.g., a high speed stirrer.

Thus, before or after washing, the silica cake is comminuted and then dried by any known means. Drying can be carried out in a tunnel or muffle furnace, for example, or by atomization in a hot air stream, the inlet temperature of which can range from approximately 200° to 500° C. and whose outlet temperature ranges from approximately 80° to 100° C. The residence time advantageously ranges from 10 seconds to 5 minutes.

If necessary, the dried material can be ground to provide the desired grain or particle size. This operation is carded out in a conventional apparatus, such as an impeller mill or an air jet grinder.

Improved Dentifrice Compositions.

This embodiment of the invention also features novel dentifrice compositions containing the silicas described above, or prepared by the process also described above.

The composition of the dentifrice has been described above in Embodiment I. More specifically, the improved dentifrice also includes constituents providing divalent and higher valency metal cations, those which are most typically used are zinc citrate, zinc sulfate, strontium chloride and tin fluoride.

Illustrative Examples

In order to further illustrate the present invention and the advantages thereof, the following specific examples are given, it being understood that same are intended only as illustrative and in nowise limitative.

In said examples to follow, the pH measuring protocol as a function of the conductivity and concentration, as well as the tests for measuring the compatibility of the silica with the various constituents, were carried out according to the following techniques:

pH Measurement protocol as a function Of the silica concentration and its conductivity;

Silica suspensions having increasing concentrations ranging from 0% to 25% by weight were formed by dispersing a mass 100 m of degassed, deionized water (Millipore quality). The suspensions were stirred for 24 hours at 25° C.

The pH of the suspensions and solutions obtained after centrifuging a fraction of the suspension at 8,000 r.p.m. for 40 min, and filtering on a 0.22 μm Millipore filter, were measured at 25° C. under a nitrogen atmosphere using a Titroprocessor Metrohm 672-type measuring system.

In the same manner, the conductivity of the resulting suspensions and solutions was measured at 25° C. using a Radiometer conductivity meter (CDM83) equipped with a CDC304 cell with a cell constant equal to $1\ cm^{-1}$. The conductivity is reported in μS/cm.

The suspension effect (SE) is defined as the difference in pH between the pH of a 20% silica suspension and the pH of its supernatant solution separated by centrifugation.

Measurement of compatibility with tin fluoride $SnF_2$:

(1) An aqueous solution containing 0.40% $SnF_2$ and 20% glycerine was formed by dissolving 0.40 g of $SnF_2$ and 20 g of glycerine in 79.60 g of twice distilled water.

(2) 4 g of silica were dispersed in 16 g of the solution produced in (1). The pH of the suspension was adjusted to 5 by the addition of 0.1N NaOH. The thus obtained suspension was stirred for 4 weeks at 37° C.

(3) The suspension was then centrifuged at 8,000 r.p.m. for 30 min. and the supernatant obtained was filtered on a 0.22 μm Millipore filter.

(4) The free tin concentration was determined by atomic absorption in the solution obtained in (1) and in the supernatant obtained in (3).

(5) The compatibility was determined by the following relationship:

$$\% \text{ compatibility} = \frac{\text{Sn concentration in the supernatant (3)}}{\text{Sn concentration in the solution (1)}} \times 100$$

Hereinafter, the percentage tin compatibility is designated Sn.

Measurement of compatibility with strontium chloride $SrCl_2.6H_2O$:

(1) An aqueous solution containing 1% $SrCl_2.6H_2O$ was formed by dissolving 1 g of $SrCl_2.6H_2O$ in 99 g of twice distilled water. The pH of the suspension was adjusted to 7.0 by adding 0.1N NaOH.

(2) 4 g of silica were dispersed in 16 g of the solution obtained in (1). The thus obtained suspension was stirred for 4 weeks at 37° C.

(3) The suspension was then centrifuged at 8,000 r.p.m. for 30 min. and the supernatant obtained was filtered on the 0.22 μm Millipore filter.

(4) The free strontium concentration was determined by atomic absorption in the solution produced in (1) and in the supernatant produced in (3).

(5) The compatibility was determined by the following relationship:

$$\% \text{ compatibility} = \frac{\text{Sr concentration in supernatant (3)}}{\text{Sr concentration in solution (1)}} \times 100$$

Hereinafter, the percent strontium compatibility is designated Sr.

The measurement of compatibility with fluorides and sodium and potassium pyrophosphates is as described in Embodiment I.

EXAMPLE 22

Into a reactor equipped with a temperature and pH regulating system and a propeller stirring system (Mixel), were introduced 8.32 liters of sodium silicate having silica concentration of 130 g/l and a $SiO_2/Na_2O$ molar ratio of 3.5 and 8.33 liters of soft water having a conductivity of 1 μS/cm. After beginning the stirring operation (350 r.p.m.), the thus formed sediment was heated to 90° C.

When this temperature was reached, sulfuric acid at an 80 g/l concentration was added at a constant flow rate of 0.40 l/min to adjust the pH to 9.5.

This was followed by the simultaneous addition of 45.25 l of sodium silicate at a silica concentration of 130 g/l, a $SiO_2/Na_2O$ molar ratio of 3.5 and a flow rate of 0.754 l/min, as well as 29.64 l of 80 g/l sulfuric acid. The sulfuric acid flow rate was adjusted such as to maintain the pH of the reaction medium at a constant value of 9.5.

After 60 min of addition, the sodium silicate addition was terminated and the sulfuric acid addition was continued at a flow rate of 0.494 l/min until the pH of the reaction mixture was stabilized at 8.0. During this phase, the temperature of the medium was increased to 95° C. This was followed by aging for a period of time of 30 min at said pH and 95° C. During aging, the pH was maintained at 8 by adding acid. Upon completion of the aging, the pH was adjusted to 3.5 by adding sulfuric acid and this pH value was maintained for 30 min.

After the heating was discontinued, the mixture was filtered and the filter cake obtained was washed with 20 l of deionized water and heated to 80° C. The cake obtained after washing was dispersed in deionized water to form a suspension having a silica concentration equal to 10%.

This was followed by a second filtration with water washing, such as to adjust the conductivity to 500 μS/cm. The cake was next washed with water having a pH adjusted to 5 by citric acid, such as to adjust the pH to a value below 6. A final washing with deionized water was then carried out.

The pH of the aqueous suspension of the disintegrated cake, having a 20% $SiO_2$ content, satisfied the following relationship:

$pH \leq 8.20 - 0.91 \log (D)$

The silica was dried by atomization. It was then ground using an impeller mill to produce a powder, the average agglomerate diameter of which, measured on a Coulter counter, was 8 μm.

The physicochemical characteristics of the thus obtained silica are reported in the following table:

| | |
|---|---|
| BET surface, m²/g | 65 |
| CTAB surface, m²/g | 60 |
| DOP absorption, ml/100 g of silica | 125 |
| Pore volume, Hg, cm³/g | 2.1 |
| pH (5% water) | 6.2 |
| Refractive index | 1.450 |
| Translucency % | 90 |
| $SO_4^=$ ppm | 100 |
| $Na^+$ ppm | 60 |
| $Al^{3+}$ ppm | 150 |
| $Fe^{3+}$ ppm | 100 |
| $Ca^{2+}$ ppm | 10 |
| $Cl^-$ ppm | 20 |
| C ppm | 20 |

Table IV below sets forth the surface chemistry characteristics of the silica according to the invention and Table V the results of the compatibility tests with the metal cations: zinc, tin, strontium, and with the standard components of dentifrice formulations: fluoride and pyrophosphate.

EXAMPLE 23

Into a reactor equipped with a temperature and pH regulating system and a propeller stirring system (Mixel) were introduced 530 l of sodium silicate at a 135 g/l silica concentration and a $SiO_2/Na_2O$ molar ratio of 3.5 and 15 l of soft water having a conductivity of 1 µS/cm. After beginning the stirring operation (350 r.p.m.), the thus formed sediment was heated to 90° C. When this temperature was reached, sulfuric acid at a concentration of 80 g/l was added at a constant flow rate of 0.38 l/min to adjust the pH to 9.5.

This was followed by the simultaneous addition of 44.70 l of sodium silicate at a silica concentration of 135 g/l, a $SiO_2/Na_2O$ molar ratio of 3.5 and a flow rate of 0.745 l/min, as well as 25.30 l of 80 g/l sulfuric acid. The sulfuric acid flow rate was adjusted such as to maintain the pH of the reaction medium at a constant value of 9.5.

After 60 min of addition, the sodium silicate addition was terminated and the sulfuric acid addition was continued at a flow rate of 0.350 l/min until the pH of the reaction mixture was stabilized at 7. During this phase, the temperature of the medium was increased to 95° C. This was followed by aging for 30 min at this pH and at 95° C. During aging, the pH was maintained at 7 by adding acid. Upon completion of the aging step, the pH was adjusted to 4 by adding sulfuric acid and this pH was maintained for 30 min.

After discontinuing heating, the mixture was filtered and the filter cake obtained washed with deionized water until a filtrate was produced having a conductivity of 2,000 µS/cm.

The cake was then disintegrated in the presence of water to form a 20% silica suspension.

A final washing stage was carried out using deionized water, such that the pH of the aqueous suspension of the disintegrated cake having a 20% $SiO_2$ content satisfied the following relationship:

$$pH \leq 8.20 - 0.91 \log(D).$$

The silica was dried at 120° C. for 24 hours and then ground on an impeller mill to produce a powder, the mean agglomerate diameter of which was 8 µm.

The physicochemical characteristics of the thus obtained silica are reported in the following table:

| | |
|---|---|
| BET surface, m²/g | 85 |
| CTAB surface, m²/g | 80 |
| DOP absorption, ml/100 g of silica | 150 |
| Pore volume, Hg, cm³/g | 3.20 |
| pH (5% water) | 6.5 |
| Refractive index | 1.455 |
| Translucency % | 70 |
| $SO_4^=$ % | 0.5 |
| $Na^+$ % | 0.05 |
| $Al^{3+}$ ppm | 250 |
| $Fe^{3+}$ ppm | 120 |
| $Ca^{2+}$ ppm | 50 |
| $Cl^-$ ppm | 20 |
| C ppm | 5 |

The following Table IV sets forth the surface chemical characteristics of the silicas according to the invention described in Examples 22 and 23. It also reports the result of the compatibility of the silicas according to the invention with the metal cations zinc, tin, strontium and with the conventional components of dentifrice formulations, namely, fluoride and pyrophosphate.

For comparison purposes, Tables IV and V also report the characteristics and compatibilities of commercially available silicas, the following list constituting a representative range of standard silicas:

Si1: Syloblanc 81 (GRACE)

Z113 : Zeodent 113 (HUBER)

Sid12: Sident 12 (DEGUSSA)

Sy115: Sylox 15 (GRACE)

T73 : Tixosil 73 (RHONE-POULENC)

T83 : Tixosil 83 (RHONE-POULENC).

TABLE IV

| Silica | Physicochemical characteristics of silicas | | | |
|---|---|---|---|---|
| | pH log (D) | SE | Ho | ZCP |
| S81 | 7.0–0.62 z | –0.17 | ≦2 | 2.2 |
| Z113 | 10–1.0 z | –0.70 | ≦3 | 2.5 |
| Sid12 | 8.5–0.60 z | –0.20 | ≦3 | 2.8 |
| Sy115 | 9.2–0.74 z | –0.94 | ≦3 | 2.5 |
| T73 | 10–0.87 z | –0.20 | ≦3 | 3.0 |
| T83 | 8.6–0.60 z | –0.18 | ≦3 | 2.5 |
| Example 22 | 8.0–0.50 z | –0.00 | ≦4 | 4.2 |
| Example 23 | 7.4–0.30 z | –0.03 | ≦4 | 4.0 |

The definitions of the symbols used in the above table are given below:

pH/log (D) represents the equation pH=b–a log (D), in which b and a are two constants and D is the conductivity of the silica suspension in µS/cm;

SE represents the suspension effect measured by the relation SE=pH suspension–pH supernatant defined above;

Ho is the Hammett constant;

ZCP represents the pH at which the surface charge of the silica is zero.

TABLE V

| Silica | Compatibilities of silicas with active molecules: % Compatibilities | | | | |
| --- | --- | --- | --- | --- | --- |
| | Zn | Sn | Sr | F | $P_2O_7$ |
| S81 | 0 | 25 | 20 | 90 | 80 |
| Z113 | 0 | 15 | 10 | 95 | 90 |
| Sid12 | 10 | 25 | 20 | 90 | 80 |
| Sy115 | 0 | 10 | 10 | 90 | 80 |
| T73 | 20 | 15 | 10 | 90 | 90 |
| R83 | 10 | 10 | 10 | 95 | 95 |
| Example 22 | 80 | 60 | 90 | 95 | 95 |
| Example 23 | 85 | 75 | 95 | 95 | 90 |

The silicas according to this embodiment markedly differ from conventional silicas as a result of their physicochemical characteristics and their good compatibility with zinc, tin and strontium.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of silica particulates adapted for formulation into dentifrice compositions, having a surface chemistry as to be at least 65% compatible with guanidine values, comprising reacting a silicate with an acid to form a suspension or gel of silica, separating such silica suspension or gel, first washing said separated silica with water until the conductivity of the filtrate is at most 2,000 microsiemens.cm$^{-1}$, and then again washing said separated silica, either with water or an acid solution.

2. The process as defined by claim 1, comprising again washing said separated silica with a solution of an organic acid.

3. The process as defined by claim 2, said organic acid comprising a carboxylic, dicarboxylic, aminocarboxylic or hydroxycarboxylic acid.

4. The process as defined by claim 3, said organic acid comprising acetic, gluconic, tartaric, citric, maleic or glyceric acid.

5. The process as defined by claim 1, comprising aging the suspension or gel of silica prior to the separation thereof.

6. The process as defined by claim 1, comprising adding an alkaline earth metal salt to said suspension or gel of silica, or to said separated silica.

\* \* \* \* \*